United States Patent
Rheinhardt et al.

(10) Patent No.: US 6,328,700 B1
(45) Date of Patent: Dec. 11, 2001

(54) LOCATING MARKER/TRACER ELEMENTS DETECTABLE BY NEUTRON ACTIVATED ANALYSIS WITHIN OR ON CARRIER MICROSPHERES, INCLUDING MICROSPHERES USED IN BIOLOGICAL EXPERIMENTATION

(76) Inventors: Christopher Rheinhardt, 31 Henshaw St., Worcester, MA (US) 01601; W. Scott Kemper, 3334 Buena Vista St., San Diego, CA (US) 92129

( * ) Notice: Subject to any disclaimer, the term of this patent is extended or adjusted under 35 U.S.C. 154(b) by 0 days.

(21) Appl. No.: 09/351,031

(22) Filed: Jul. 9, 1999

(51) Int. Cl.[7] ........................................................ A61B 5/02
(52) U.S. Cl. ................................ 600/504; 600/505; 600/3
(58) Field of Search .............................. 600/1–8, 504–505

(56) References Cited

U.S. PATENT DOCUMENTS 5,302,369 * 4/1994 Day et al. .............................. 600/3 X
6,099,457 * 8/2000 Good ........................................ 600/8

* cited by examiner

*Primary Examiner*—John P. Lacyk
*Assistant Examiner*—Ryan Carter
(74) *Attorney, Agent, or Firm*—Fuess & Davidenas

(57) ABSTRACT

Microspheres are permanently marked with non-radioactive stable isotopes of elements suitably detected by neutron activation analysis. The marked microspheres are suitable to permanently label diverse things. For example, families of stable-multiple-isotope-marked microspheres injected into an animal become lodged by the circulating blood within selected tissues of an animal during blood flow analysis experimentation. Absolute and relative abundances of these stable-isotope-marked microspheres residing within harvested tissues are readily accurately automatically measured in situ within the harvested tissue samples by neutron activation analysis. The quantitatively measured abundance of the isotopes, and associated microspheres, are accurately indicative of the former flow of blood containing the microspheres to the tissue. Microspheres are preferably marked with stable isotopes of gold, antimony, lanthanum, samarium, europium, terbium, holmium, ytterbium, lutetium, hafnium, tantalum, tungsten, rhenium, osmium, iridium, scandium and/or bromide.

22 Claims, 3 Drawing Sheets

Table 1: Theoretical estimate of sensitivity

| Element | Reaction | $t_{1/2}$ | $\sigma$ | f | Specific Activity |
|---|---|---|---|---|---|
| Samarium | $^{152}Sm(n,\gamma)^{153}Sm$ | 1.92 d | 208 | 26.7 | $2.1 \times 10^{12}$ ds$^{-1}$kg$^{-1}$ |
| Lanthanum | $^{138}La(n,\gamma)^{139}La$ | 1.69 d | 9 | 99.9 | $3.9 \times 10^{12}$ ds$^{-1}$kg$^{-1}$ |
| Iridium | $^{193}Ir(n,\gamma)^{194}Ir$ | 170 d | 1500 | 62.7 | $4.9 \times 10^{10}$ ds$^{-1}$kg$^{-1}$ |
| Antimony | $^{121}Sb(n,\gamma)^{122}Sb$ | 2.70 d | 5.9 | 57.4 | $1.4 \times 10^{11}$ ds$^{-1}$kg$^{-1}$ |
| Ytterbium | $^{174}Yb(n,\gamma)^{175}Yb$ | 4.19 d | 100 | 31.8 | $1.1 \times 10^{11}$ ds$^{-1}$kg$^{-1}$ |
| Lutetium | $^{176}Lu(n,\gamma)^{177}Lu$ | 6.68 d | 2300 | 2.6 | $9.5 \times 10^{11}$ ds$^{-1}$kg$^{-1}$ |
| Gold | $^{197}Au(n,\gamma)^{198}Au$ | 2.70 d | 98.7 | 100 | $2.6 \times 10^{12}$ ds$^{-1}$kg$^{-1}$ |
| Rhenium | $^{185}Re(n,\gamma)^{186}Re$ | 3.78 d | 112 | 37.4 | $9.6 \times 10^{11}$ ds$^{-1}$kg$^{-1}$ |

Figure 3

LOCATING MARKER/TRACER ELEMENTS DETECTABLE BY NEUTRON ACTIVATED ANALYSIS WITHIN OR ON CARRIER MICROSPHERES, INCLUDING MICROSPHERES USED IN BIOLOGICAL EXPERIMENTATION

BACKGROUND OF THE INVENTION

1. Field of the Invention

The present invention generally pertains to chemical or elemental markers or tracers that, when combined with other chemical admixtures or compounds, or when inserted into or upon objects or devices, thereafter serve to permanently identify such admixtures, compounds, objects or devices, including after such change(s) and gross change(s) to the compounds, objects or devices in form and/or in composition as may be occasioned by lapse of. time, dissipation, wear, deterioration, oxidation, or explosion.

The present invention particularly concerns (i) elemental or chemical markers that are indefinitely long lasting, and detectable at the level of a single atom or molecule over a fast range of densities; (ii) the use of neutron activation in the detection of elemental and chemical markers, and the elemental or chemical markers so detectable; and (iii) the packaging of, and/or carriers for, neutron-activation-detectable elemental and/or chemical markers, including the packaging of elemental and/or chemical markers in carrier microspheres, including microspheres as are used in biological experimentation including, inter alia, in blood flow analysis.

2. Description of the Prior Art
2.1 Neutron Activation Analysis

The present invention will be seen to employ neutron activation analysis.

Individual stable elements (e.g., gold) are known to have isotopes that are strongly detectable by neutron activation analysis. The known abundance of the "marker" elements in certain substances has permitted these elements to serve as markers for the substances. See Kennelly, J. J., Apps, M. J., Turner, B. V. and Aherne, F. X. 1980; *Dysprosium, cerium and chromium marker determination by instrumental neutron activation analysis*. Can. J. Anim. Sci. 60:749–761. See also Nishiguchi Y., Sutoh M., Nishida T., Satoh H., Miyamoto S.; *Neutron activation analysis of Lanthanides (La, Sm and Yb) as a particle marker, and estimation of passage rates*. Anim. Sci. Technol. (Jpn.), 67: 787–793. 1996.

Neutron activation analysis can provide the life science community with capabilities not readily available with other assay technologies. Neutron activation is well known for both (i) its excellent sensitivity and (ii) its specificity for the simultaneous measurement of multiple elemental trace elements. This specificity offers the potential of being able to measure multiple isotopic tracers per assay.

Unlike light, neutrons can penetrate solid tissue and opaque-liquid samples, thereby providing an assay that is completely self-contained with but minimal sample preparation.

Unlike other element detection methods, such as atomic absorption spectrophotometry, neutron activation is not chemically or physically destructive. Therefore, samples can be archived, re-assayed, and/or undergo additional chemical analysis following neutron activation.

Because only the samples of interest are neutron activated, assay by neutron activation analysis can significantly reduce-occupational exposure to radiation and eliminate the low-level radioactive waste generated. For example, the contamination of gloves and protective clothing, glass and plastic laboratory supplies, and waste products from research animal housing and carcasses attendant upon the use of radioactive tracers are completely avoided. Stable isotopes do not undergo further radioactive decay or cause radiokinistics and, unlike some colorometric probes, they do not suffer any loss of activity (i.e., loss of fluorescence) over time. Therefore, stable isotope labeled products will have an indefinitely long shelf life: significantly longer than competing labeling methods.

The major disadvantage to assay by neutron activation technology is the required access to a neutron source. If the neutron radiation source is to be strong (i.e., with a high flux) so that it will excite a significant proportion of the target tracers—preferably stable isotopes—of the sample—which sample may be sparse—to an excited, radioactive, energy level in a reasonable time, providing thereby a reasonable population of radionuclides the decay of which may likewise be detected during a reasonable time, then the source of neutron flux must most commonly be energetic, as is typically derived from a research reactor. Suitable research reactors, and reactor time, are not scarce in the United States circa 1999. However, the reactors are located at particular sites not normally coincident with sites at which investigations in the life sciences are conducted. Therefore, samples for assay by neutron activation analysis must normally be sent to a reactor, irradiated with neutron flux, and analyzed with results being reported to the sender. Furthermore, the samples, if not permanently archived at or near the site of the reactor, may be returned to the sender only when radiation has sufficiently abated.

Accordingly, and despite the many advantages of neutron activation, this general analytical tool has not (as of 1999) reached its full potential within the life science community due to some combination of (i) a lack of user awareness of the technique, (ii) a lack or perceived lack of access to reactors, and/or, importantly to the present invention, (iii) a lack of commercially available stable-labeled research products specifically designed for neutron activation technology. These research products would desirably be targeted on intended biological research applications, and be of a form familiar to biological researchers.

Most recently, BioPhysics Assay Laboratory, Inc., 280 Wellesley Avenue, Wellesley Hills, Mass. 02481 (Phone/Fax: (781) 239-0501) ["BioPAL"] has been formed to (i) develop, manufacture and market a new generation of high-precision stable-labeled research products, and to (ii) provide a state-of-the-art assay service that can meet commercial demand. The present invention will be seen to concern these stable-labeled research products, developed jointly with Triton Technology, Inc., of San Diego, Calif.

In passing, it should be noted that neutron activation analysis also has an extensive history in the detection of explosives—which is a different thing than the detection of stable isotopes, used as makers, that may be placed into, inter alia, explosives as will be taught by the present invention. In other words, certain chemicals present in certain explosives can be directly detected by neutron activation analysis. As a leading book on this topic, see *Explosive detection using fast neutron activation analysis* by Terry E. Carrell, published by North American Rockwell, Los Angeles, Calif.

When the present invention is later understood to be stable-isotope labeled microspheres usable as markers in diverse circumstances, it will be useful to consider the possible use of these markers in labeling explosives. Stable-isotope labeled microspheres serving as identifying markers cannot be assured to be emplaced in explosives save those legitimately produced, and then only under mandate of law or regulation.

However, in accordance with the general principles of the present invention, later explained, to the effect that the carriage, and the chemistry, of the marker stable isotope is divorced from the chemistry of the exterior surface of a microsphere which serves to mechanically retain the marker stable isotope, it can be anticipated, in advance, that ubiquitous, tailored, stable-isotope labeled microspheres in accordance with the present invention will be very useful for permanently marking an immense number of different admixtures, compounds, objects or devices, including, inter alia, explosives. Properly tailored to a target, including an explosive, about the only way of expunging microspheres and any elemental markers that they contain from a compound such as an explosive is by gross molecular dissociation such as is characteristic of, inter alia, explosion. Of course, to remove the microspheres, and markers, requires destruction of the compound. Moreover, such explosion and attendant molecular dissociation does not truly get rid of the elemental markers, which remain (and will remain, short of atomic transmutation) as residue.

It will next immediately be discussed that microspheres may be both (i) mechanically and/or (ii) chemically, tailored, or "targeted", to their intended environment of use. Most of this discussion will involve prior art biological uses of microspheres. Stable-isotope labeled microspheres will later be seen to be fully as susceptible of being "targeted" upon an intended environment of use as were previous microspheres. Moreover, and recalling the requirements of labeling explosives, it should be appreciated in considering the diverse labeling and marking requirements of the prior art (both biological and non-biological), that the "targeting" of stable-isotope labeled microspheres in accordance with the present invention on an intended environment of use will prove to be selectively either broad or narrow, and semi-permanent or permanent, all in accordance with (i) application requirements and (ii) the principles of chemistry.

2.2 Types of Microspheres, Circa 1999

The mechanism of the present invention for delivering stable elements that are suitable to form isotopes detectable by neutron activation analysis will be seem to be: microspheres.

"Microspheres" is the generic term applied to certain minute, typically homogeneous and uniformly-size-graded, particles, beads or whatever existing in over 2000 types. The microspheres are commonly made of latex rubber, polystyrene (PS) plastic, or other polymers, copolymers, terpolymers, and silica. They come in a variety of densities from 0.9–2.3 g/ml. They come in a sizes ranging from nanometers to millimeters.

Microspheres are both (i) mechanically and (ii) chemically versatile; properties of which good utility will later be seen to be made in the present invention.

A broad range of sizes and types or microspheres—also known as uniform latex particles—are available from commercial sources. For example, diverse microspheres are available from Bangs Laboratories, Inc., 979 Keystone Way, Carmel, Ind. 46032. Microspheres are available in diameters from ~0.020 $\mu$m (20 nm) to 1000 $\mu$m (1 mm). Size uniformity is excellent: c.v.'s are typically <3%, and are often ~1%.

Colored and fluorescently-colored microspheres are available from said Bangs Laboratories, Inc., from Triton Technologies, Inc., and from Molecular Probes, Inc. in a spectrum of colors. More than 300 different dyed microspheres are available in colors from red to beyond violet, as well as black, white, and gray. Bright primary colors are available for easy color identification and mixing of colors; others are very dark, like ink, for good contrast.

Microspheres may be obtained that are dyed with fluorescent dyes. More than 30 different-sized microspheres colored with >10 different absorbance and fluorescent dyes exhibiting various excitation and emission wavelengths are commercially available.

Microsphere surface chemistries range from hydrophobic (plain polystyrene) to very hydrophilic surfaces imparted by a wide variety of functional surface groups: 1) aldehyde —CHO; 2) aliphatic amnine —CH2—NH2; 3) amide —CONH2, 4) aromatic amine-NH2; 5) carboxylic acid —COOH (3 different types); 6) chloromethyl —CH2—Cl; 7) epoxy; 8) hydrazide —CONH—NH2; 9) hydroxyl —OH; 10) sulfate —SO4; and 11) sulfonate —SO3.

The original recipe for various types of ~1 $\mu$m (100 nm) diameter COOH— or —NH2 modified microspheres contained 12, 20, 40, or 60% magnetite. Truly superparamagnetic, these microspheres respond to a magnet but display no residual magnetism. These microspheres can be used for direct adsorption. of proteins, or surface groups can be used for covalent coupling of ligands (proteins, DNA, etc.)

The narrow size distribution type were designed for better performance in cell depletion applications. Encapsulated microspheres have a magnetite-rich core and a polystyrene shell, with COOH and NH2 surface groups. These microspheres make better solid supports for applications using enzymes because there is no iron on the surface.

As an example of microspheres with attachments, the Pro active Streptavidin coated superparamagnetic beads of Molecular Probes, Inc., serve as a generic magr.et.ically responsive solid phase to which a variety of biotinylated items can be attached. The Pro active Protein A coated magnetic microspheres provide an IgG-binding affinity support that is extremely easy to manipulate.

For example, Pro active GAM magnetic microspheres having goat anti-mouse Fc-specific IgG serve to bind mouse IgG's and orient the mouse IgG's correctly for high activity with less- primary Ab.

Streptavidin, protein A, and GAM coated non-magnetic, polymeric microspheres are also available in several sizes. Some of the more common applications of protein-coated microspheres include: (i) affinity chromatography, (ii) multi-purpose solid phase for immunoassays, (iii) nucleic acid hybridization, (iv) immunoselective cell separation, and (v) DNA sequencing.

For purposes of the present invention, it should only be understood that microspheres can both (i) mechanically carry diverse elements within their matrix—for example, ferromagnetic iron—and can (ii) chemically affix diverse chemical compounds, including those of biological interest. Both the (i) mechanical and (ii) chemical combinations can be relatively permanent, essentially demanding a destruction of the microsphere (which may not be easy) in order to sever the association.

2.3 Uses Of Microspheres, Circa 1999

2.3.1 Blood Flow Analysis

Microspheres of both the radioactive and the non-radioactive, absorbance-dye and fluorescent-dye labeled, types are regularly used in the measurement and analysis of in vivo blood flow or, more particularly, regional myocardial blood flow (RMBF). Such microspheres are also used in measurement of the flow of gas in the lungs, or the movement of materials through the gut, or like fluid movement processes occurring within the higher animals.

As regards the use of radioactive-labeled microspheres, their presence is detected with detectors of gamma radiation emitted during decay events.

As regards the use of non-radioactive absorbance-dyed or fluorescently-dyed microspheres, the dyes used to mark the microspheres may be, in different variants, either elutable to non-elutable, with the dye absorbance or fluorescence measured in various ways, including in bulk by the use of automated or semi-automated absorbance or fluorescence detector equipments.

2.3.2 Latex Agglutination Tests and Particle Immunoassays

Many microspheres are used in various medical diagnostic applications. Proteins will adsorb readily onto polystyrene (PS) microspheres or they may be covalently coupled to. carboxylic acid or other surface functional groups. Microspheres so coated with antibodies can be agglutinated (agglomerated) by the appropriate antigens.

2.3.3 Sandwich Assays and Tests (Particle Capture ELISA's)

Antibody-coated microspheres form the basis for particle capture ELISA tests and related assays (i.e., those that form a blue dot). Antigen links the sandwich of (1) primary antibody-coated particle and (2) enzyme-labeled secondary antibody. Microspheres permit easy preparation of reagents (antibody coating of microspheres done in bulk, not on a membrane) and precise placement of Ab-coated microsphere spots on top of the filters.

2.3.4 Dyed Particle Sandwich or Chromatographic "StripTests"

Darkly dyed microspheres can eliminate the need for enzymes (and their attendant stability problems) in sandwich assays. Tests use dyed microspheres attached to one of the two sandwich antibodies. Small, antibody-coated microspheres move easily through the membrane in chromatographic-like assays; deeply dyed (some as dark as ink!), they bring enough color to the sandwich to completely preclude the use of enzymes. A wide variety of colors are available, including bright fluorescents.

2.3.5 NIST-traceable Standards

Calibrated uniform diameter microspheres for use as standards and controls for particle or cell counting and measuring instruments are available singly or in sets.

2.3.6 LDV/PIV Seeds

Microspheres have been used as seed in fluid flow streams for laser Doppler and particle image (and other) velocimetry measurements. In these applications they maybe dispersed in gas streams, wind tunnels, wave tanks, or ship tow-tanks. Silica microspheres permit use in combustion studies and other high temperature applications, too.

2.3.7 Other Applications

Other applications for nicrospheres include 1) blood cell simulation; 2) cell separation; 3) phagocytosis studies; 4) chemiluminescent assays; 5) column packing (non-porous); 6) density calibrators; 7) DNA probes/ PCR; 8) instrument standards; 9) fluidized beds; 10) magnetic resonance imaging; 11) model studies; 12) solid phase DNA sequencing; 13) spacers for flat panel displays; and 14) void sources for ceramics.

Applications for dyed microspheres include 1) stains; 2) adjuvants; 3) contrast agents; 4) cell tags (rosettes); 5) gel permeation markers; 6) flow markers for liquids; and 7) confocal microscopy standards.

2.4 Methods of Using and Measuring Microspheres, Circa 1999

General background to the present invention as regards the use of microspheres in biological measurements may be found in U.S. Pat. No. 5,230,343 for COLORED MICROSPHERES FOR MEASURING AND TRACING FLUID MIXING AND FLOW, PARTICULARLY BLOOD FLOW TO TISSUE to inventors Gerd Heusch, Michael P. Guberek, and W. Scott Kemper; in U.S. Pat. No. 5,253,649 for a PROCESS FOR THE MEASUREMENT OF BLOOD CIRCULATION BY MEANS OF NON-RADIOACTIVE MICROSPHERES to inventors Gerd Heusch, Rainer Gross, Wolfgang Paffhausen and Andreas Schade; and in German patent application Serial No. P 40 19 025.0 filed in Germany on Jun. 14, 1990 which is the priority application to both these patents. All these related patents are assigned to Triton Technology, Inc., of San Diego, Calif., a corporation of the State of California. The contents of the related patents are incorporated herein by reference.

2.4.1 Use of Microspheres in Fluid Flow Analysis

Traditionally, most measurements of fluid mixing and fluid(s) flow(s) are direct. One or more fluid flows may simply be measured while such flows are occurring. Alternatively, any mixture that results from the flows of two or more fluids may be analyzed as to its constituent components in order to quantitatively determine the fluid flows that have transpired.

However, direct measurement of fluid(s) flow(s), such as within the blood stream of a living animal, is often impossible. Moreover, direct quantitative analysis of the constituent components of complex, or extensive, mixtures of fluids is often prohibitively difficult or expensive. The expense is magnified if many samples must be taken, and analyzed, over time.

Accordingly, modeling or simulation is sometimes used in order to trace the flow, and mixing, of one or more fluids. For example, a dye may be put in ground water and its dispersion may subsequently be observed. From the observed dispersion of the dye a similar dispersion of pollutants, or other less readily detectable fluids, may be imputed.

Another, relatively sophisticated, form of fluid flow and fluid mixing analysis is indirect. A physical marker is put into, or a chemical marker is bonded to, an actual fluid, or a fluid component, for which flow and/or mixing is desired to be assessed. The fluid serves as a carrier. When the distribution of the marker is analyzed then the corresponding distribution of the carrier fluid is imputed.

The highest, and most exacting, expression of this indirect method is in medicine, and particularly in blood flow analysis. The blood, and the organs and tissues receiving blood, within a living animal present a system that is very complex in its fluid flow patterns and dynamics, and that is difficult of direct access and measurement. Accordingly, microscopic markers are placed by catheter into the left atrium of the animal's heart, entering into the animal's blood thoroughly mixed where they are subsequently distributed to the animal's tissues in proportion to the blood flowing to the tissues.

The microscopic markers are commonly microspheres sized (typically less than 30 $\mu$m and more than 7 $\mu$m and more typically 15 $\mu$m) so that they are trapped by, and permanently lodge within, the smallest capillaries of the animal's tissues. In proportion to the flow of blood, the particles are sized so that they are trapped in the capillaries on their first pass through the circulation system of the animal. The tissues are subsequently harvested, and the prevalence—i.e., the numbers—of the markers have previously been analyzed, producing thereby an indirect indication of the blood flow to the tissue.

Previous systems developed for medical blood flow analysis—discussed in greater detail hereafter—have proven to be both complex and expensive. Because of their cost and complexity, such systems have not been found suitable for use in routine industrial or environmental fluid flow and mixing measurement problems.

However, it should be recognized that the flow of blood, or blood components, within the arteries and veins of a living animal is only different in complexity, and not in the essential nature of fluid flow dynamics, from the flows of fluids occurring within factories, ecosystems, and the like. Accordingly, if a reliable, effective, inexpensive, and automated (or semi-automated) indirect fluid flow measurement system suitable for use on the difficult problem of blood flow analysis could be developed, then such a system might well have general applicability to the tracing and measurement of fluid flows, and the mixing of fluids, in many other diverse applications.

2.4.2 The Earliest Measurements of Blood Flow with Radioactive Microspheres

The reasons for the measurement of blood flow are set forth in U.S. Pat. No. 4,616,658 to Shell, et. al., for NON-RADIOACTIVELY LABELED MICROSPHERES AND USE OF SAME TO MEASURE BLOOD FLOW. Shell and his co-inventor See teach a safe and inexpensive method of measuring blood flow in experimental animals using non-radioactively labeled microspheres is provided. The microspheres may be comprised of a variety of materials, including latex and agarose, and may be labeled with colored dyes or by linkage to enzymes, plant enzymes being preferred because they do not occur naturally in an animal's system. After injection and circulation of the microspheres throughout the animal's system, blood flow to particular tissue may be. measured by counting the number of microspheres in the tissue sample, the initial number of microspheres in the animal's blood stream having been measured shortly after injection. In the case of microspheres labeled with colored dyes, the spheres may be counted in tissue either after separation from the tissue or while still trapped in the tissue's capillaries. Techniques for separating the microspheres from blood and tissue are also provided.

The measurement of blood flow in experimental animals is often necessary in the fields of pharmacology, physiology, therapeutics and diagnostics. For example, toxicology studies require blood flow measurement to determine the toxicity of various suspected toxic agents. Further, many diagnostic and therapeutic advances have some impact on the flow of blood. It is therefore desirable to take blood flow measurements.

Blood flow measurements can be performed in many anatomical areas, including the brain, heart, lung, gut, kidney, reproductive organs, skin and muscle. One sensitive and specific previous technique involves the use of radioactively labeled microspheres. In one variant of the technique plastic or polystyrene microspheres are marked with a radioactive label and injected into the left atrium of the heart of an experimental animal. They are injected into the left atrium in order to achieve homogeneous mixing of the spheres in the blood. The prevalence of the radioactively-labeled microspheres in the blood is assessed by withdrawal of a blood sample from the aorta downstream from the heart, during the complete course of the atrial injection. This "reference withdrawal" sample is used to determine the "radioactivity per volume flow rate" of the blood coming from the heart. The mixed microspheres disperse in proportion to blood flow and lodge in the micro-capillaries within the tissues of the animal. The animal is later sacrificed and the organ(s) of interest is (are) harvested. Blood flow to a particular organ is determined by measuring the level of radioactivity in the organ sanple, which radioactivity is a function of the number of microspheres trapped in each portion of the organ. This radioactivity level is divided by the reference withdrawal value in order to determine absolute blood flow.

Notably, the radioactive strength, or intensity, of the injected microspheres is not required to be exactly known. Ultimately only ratios between the (i) density of injected microspheres, and (ii) the density of microspheres recovered from each tissue, will prove relevant. To start, blood is withdrawn at a predetermined rate from a site downstream from the point of injection for a longer time than it takes for all the injected microspheres to pass this point. Only a small fraction of the flowing blood, and a commensurately small fraction of the microspheres contained within the blood, are extracted. However, the density of the microspheres within the blood is directly determinable in terms of units radioactivity (i.e., radioactive intensity) per unit measure of blood flow rate (volume per unit time). Notably, it is not necessary to calculate the numbers of microspheres per unit blood—although this number may also be determined.

Later, when the animal's tissue samples are harvested, each tissue sample obviously contains but a minute fraction of the millions of injected microspheres that are now lodged within, and blocking, of a corresponding number of minute capillaries of the billions of such capillaries within the animal's entire body. The intensity of microspheres within the harvested tissue may likewise be expressed in terms of units radioactivity (i.e., radioactive intensity) per unit measure of volume or of weight. Dividing the harvested radioactive intensity by the injected intensity causes the specific radioactive strength of the microspheres to cancel out of the equation, and the volume blood flow (normally expressed in ml/min/gm) reaching the organ of interest is directly determined. Prior art dye-elution microspheres, which will be later discussed, work on the same principle.

Dye-colored microspheres are better adapted to long term quantification than are radioactive microspheres once a microsphere is (quantitatively) color-dyed as it then holds the dye, without appreciable change, during all conditions of storage and passage through the bloodstream.

2.4.3 Limitations of Conventional Radioactive Microspheres

The main (but not the only) problem with radioisotope-labeled microspheres is shelf life. In order that the decay events from the radioisotopes should be detectable during the lapse of a reasonable period of time, the radioisotopes must have short half-lives. A radioisotope lodged on a "radioactive microsphere" commonly has a radioactivity "half-life" that is as short as several days and no longer than a few weeks or months; the intensity of the radioactive emission from the radioactive microsphere decreasing by half with each passing of the "half life" period. Since radioactivity decays with time, it becomes necessary to inject larger and larger numbers of aged microspheres to permit that the microspheres should still be reliably detectable.

A supply of radioactive microspheres ages even while they are on the shelf. Radioactive microspheres thus have a time limited shelf life, which adds a cost factor to their use. The problem of decreasing radioactive intensity does not end with injection into an animal. Care must also be taken not to let too much time go by before harvesting and analyzing the tissue samples or there may be insufficient activity to determine low fluid flows due to the 'noise' threshold of a typical gamma counter used for measurement of radioactivity. Constant replenishment, inventory management, and renewal of microspheres used in, principally, biological experimentation is an onerous laboratory task. If not performed diligently experimental schedules may be disrupted. Although due precautions are taken in transport and storage of radioactive microspheres, the constant flux of newly produced radioisotopes from manufacturer to laboratory, the controlled storage of radioisotopes still suitable for experimental use, and the long term of radioisotopes no longer suitable for use but still sufficiently radioactive so as to be unsuitably released into the environment, all involve a biohazard.

The present invention will be seen to avoid this problem entirely; all isotopes being distributed, stored, used, optionally stored again, and re-shipped in a non-radioactive form over an indefinitely long time period with an arbitrarily long duration in each phase. Meanwhile, the high sensitivity and specificity of radioactive labeling will be seen to be preserved.

Still other problems and disadvantages associated with radio-isotope labeled microspheres will be seen to be eliminated or substantially abated.

First, the high start-up costs of using radioactive isotopes will be seen to be avoided. These costs commonly include special government licensing, and purchase and maintenance of each of a gamma counter to measure radioactivity, shielding to protect laboratory workers from radiation exposure, and complex storage facilities. There is typically a high minimum "per order" cost of equipments from manufacturers. These high costs severely limit the use of radioisotope-labeled microspheres in blood flow measurement, generally restricting its use to large laboratories and medical centers.

Second, because of the half-lives of their contained radioisotopes, radioactively-labeled microspheres have a limited shelf life typically ranging from weeks-to several months.

Third, because of the short half-lives of many radioisotopes, radioactively-labeled microspheres are typically usable only in experiments of durations that are no more than a few weeks or months.

Fourth, commercially available automated gamma-ray counting equipment is NaI-based. Sodium-iodine (NaI) crystals provide a low-cost, sensitive gamma-ray counting system with intrinsically poor spacial resolution. As a result, researchers are limited in the number of different radioactive microspheres that can be accurately measured per sample, due to overlap between the emission energies of available radiolabels. Typically, researchers are limited to five radiolabels. Increasing the number of radiolabels measurements is done only at a significant loss in sensitivity and specificity. (The measurement of the separate radioactively-determined blood flows is performed by mathematically-based techniques. Namely, "matrix-inversion" analysis is performed to remove the known "spill-over" between the emission spectra of various emitting species. A "cross-over" matrix is mathematically solved. These techniques are similar to the spectrographic analysis of a palette of dye-colored microspheres.)

Fifth, laboratory workers using radioactively-labeled microspheres are exposed to radiation danger. The radioactively-labeled microspheres are especially dangerous if they enter into the human body by ingestion, respiration, or accidental injection. They are so small, and so numerous, so as to be incapable of removal. Accordingly, the costs, and risks, involved in minimizing radiation exposure can be substantial.

Sixth, licenses are required form various local, state, and national Governmental regulatory agencies in order to transport, possess, use, and dispose of radioactive materials, including radioactively-labeled microspheres.

Finally, and perhaps most critically, disposal of the experimental animals poses significant problems, both logistically and financially. Because the entire animal carcass remains radioactive for some time after use, and must be placed in a special low level radiation dump, to which dumps there is increasing public antipathy. The cost of disposal is becoming prohibitively high, recently ranging to as high as $750 U.S. or more per animal.

2.4.4 The Earliest Measurements of Blood Flow With Colored Microspheres

Colored microspheres are primarily relevant to the present invention for showing (i) the increased flexibility in experimental procedures that may be realized when radioisotope-labeled microspheres need not be timely extracted and measured, and (ii) the powerful ways by which, adequate time being had with no danger from radiation, the microspheres can be chemically and even mechanically tailored on a particular experimental protocol.

In 1967, polystyrene latex, radioactively-labeled microspheres (RM) were introduced for the measurement of regional perfusion. See Rudolph A M, Heymann Mass.: The circulation of the fetus in utero: Methods for studying distribution of blood flow, cardiac output and organ blood flow. Circ Res 1967; 21:163–184.

One year later, Makowski, et al., introduced a blood withdrawal technique for the quantifying of regional blood flow. See Makowski E L, Meschia G, Droegemueller W, Battaglia F C: Measurement of umbilical arterial blood flow to the sheep placenta and fetus in utero: Distribution to cotyledons and the intercotyledonary chorion. Circ Res 1968; 23:623–631.

In 1969, Domenech, et al., first validated the use of radioactive microspheres (RM) for the measurement of regional myocardial blood flow (RMBF). See Domenech R F, Hoffman J I E, Noble M I M, Saunders K B, Henson J R, Subijantos: Total and regional coronary blood flow measured by radioactive microspheres in conscious and anesthetized dogs. Circ Res 1969; 25:581–596. Thereafter, this method has become the standard technique for the measurement of RMBF in various experimental settings. However, due to the precautionary measures needed to minimize radiation exposure, use of RM is restricted to specially licensed laboratories. As mentioned above, storage of the radioactive microspheres, as well as disposal of radioactive waste, is expensive and presents a health and environmental hazard.

To avoid some of these limitations inherent to the RM method, U.S. Pat. No. 4,616,658 to Shell, et al. for NON-RADIOACTIVELY LABELED MICROSPHERES AND USE OF SAME TO MEASURE BLOOD FLOW Describes a method for measuring RMBF using non-radioactive, colored microspheres (CM). Later, Hale, et al., described a similar technique. See Hale S L, Alker K J, Kloner R A: Evaluation of non-radioactive, colored microspheres for measurement of regional myocardial blood flow in dogs. Circulation 1988; 78:428–434.

According to the techniques of Shell, et al., and of Hale, et al., microspheres may be (i) labeled with colored dyes, and (ii) subsequently visually identified and counted after recovery from digested tissue, either after separation therefrom or while still trapped in the tissue's capillaries. Shell, et al. also describe labeling microspheres by linkage to enzymes, particularly plant enzymes, and, after extraction from tissue, measuring the density of enzyme-linked spheres by a measurement of colorometric density which is indicative of enzyme activity.

In the previous techniques using non-radioactively-labeled dye-colored microspheres (CM), tissue samples that have trapped, or captured, microspheres from the circulating blood of a live animal are surgically harvested after euthanasia of the animal; and are then digested by a combination of enzymatic and chemical methods. Aliquots of the microspheres trapped within a given sample are then counted in a hemocytometer by an investigator using light microscopy, or, in the case of enzyme-linked microspheres, by measurement of colorometric density to determine enzyme activity.

There are, however, significant limitations. to these previous counting techniques. First, RMBF is extrapolated from only a small aliquot of the dye-colored microspheres (CM) actually trapped within the sample, thereby entailing a substantial statistical error in RMBF calculations. Second, the use of a maximum of only three different colors (in the same experiment) has been validated in the literature, and then in only a small number of samples, whereas it is clearly desirable to be able to make more than three measurements of RMBF in many common experimental protocols. Third, there was considerable variation in the diameter of the CM used in previous studies, as admitted by Hale et al. Fourth, the prior methods require substantial time for the tedious counting of individual dye-colored microspheres. Automation for optical counting is expensive, typically $40–50 K U.S. circa. 1993. Fifth, in preliminary experiments, the inventors of the present invention found it almost impossible to distinguish visually the nine (9) commercially available microsphere colors in the reddish background of digested myocardium.

Recently, still another alternative non-radioactive method for measuring RMBF was developed by Morita, et al. using X-ray fluorescence excitation of microspheres loaded with elements of high atomic number. See Morita Y, Payne B D, Aldea G S, McWattes C, Huseini W, Mori H, Hoffman J I E, Kaufmann L: Local blood flow measured by fluorescence excitation of non-radioactive microspheres. Am J Physiol 1990; 258:H1573–H1584. So far, only two different labels have been reported to have been validated by comparison to radioactive microspheres (RM) after intracoronary injection in two dogs. The method of Morita, et al. could be hampered by leaching of the label from the microspheres over time. Another disadvantage is the need of a sophisticated and extremely expensive equipment for X-ray excitation and fluorescence detection which is not commercially available.

The previous blood flow analysis methods employing dye-colored microspheres, including the method of Morita, et al., require that the numbers of microspheres per unit portion of a recovered tissue sample should be determined. Because the numbers of microspheres introduced within the blood [typically five to ten million ($5-10 \times 10^6$)], and captured within the capillaries of the tissue, are large in the counting techniques, the actual numbers are commonly only estimated by statistical sampling, which induces measurement error. Worse, even the determination of the numbers of dye-colored microspheres that are within minute subsamples is tedious and expensive, involving in the methods of Shell, et al., and of Hale, et al., manual or semi automated observations through a microscope.

In order to circumvent these limitations, it would be desirable if a new method of producing and/or using microspheres, and of measuring RMBF therewith, could support both (i) easy tissue processing (i.e., digestion) and (ii) quantitative, automated, and easy counting of every microsphere within an individual sample. Such a new method would desirably be both economical and validated by a rigorous comparison to RM over a range of RMBF from 0 to 10 ml/min/gm on many hundreds, or thousands, of individual myocardial samples. If such a method were to be suitably economical, reliable, easy to use, and devoid of significant drawbacks, then it might find general use in the measurement and analysis of diverse fluid flow and fluid mixing problems other than only medical problems.

2.4.5 Blood Flow Measurement as Taught in the Certain Previous Patents of Assignee Triton Technology, Inc.

The predecessor patents listed in section 2.3 above, assigned to Triton Technology, Inc. of San Diego, Calif., teach advanced dye-colored microspheres, and the use thereof in blood flow measurement.

The methods of the related patents replace the "counting" of the numbers of non-radioactively labeled microspheres during a use of such microspheres in fluid flow analysis with, instead, a direct measurement of the amount of a colored, non-radioactive, dye that is carried by such microspheres. The dye is removed from the recovered microspheres by elution or by simply dissolving the spheres. The solvent is then analyzed for dye content by absorbance or fluorescence spectrophotometry. Measurement of the amount of dye accomplished directly by spectrographic methods is much easier and faster than counting the numbers of microspheres, and accounts for all the microspheres in the sample, and not just a small aliquot.

In particular, the (i) microspheres of the prior patents are dyed with a color for which the quantitative photometric absorption or emission (fluorescence) spectrum is uniquely identifiable, (ii) the labeled and dye-colored microspheres (CM) so created are introduced in a fluid flowing into a volume serving as a reservoir of such fluid, (iii) after the introduction of the CM the concentration of dye within the fluid (concentration being the amount of dye per unit portion of fluid) is determined, (iv) the CM are recovered from a complete sample, not a small aliquot of the sample volume into which the fluid containing the introduced CM has flowed, (v) the colored dye is eluted or dissolved from the recovered CM with a solvent, and (vi) the recovered dye is quantified by a spectrophotometric procedure. The relative amplitude of the photometric spectrum of the recovered dyes gives a quantitative indication of the concentration of the dyes within the sample. The concentration of dye that was within the original fluid is normally similarly determined, i.e. by spectroscopy. The ratio of these two concentrations indicates the flow of the fluid within which the CM were previously resident into the volume relative to the overall flow of fluid.

Fluorescent dye spectrum analysis offers some apparent advantages for CM applications, when compared to absorbance spectra analysis. Fluorescent dyes emit light isotopically and can be read off-axis (i.e., at 90°) from the excitation source. Because reflection of the excitation light is minimized at high angles, this serves to minimize noise in the form of extraneous light. The complete emission spectra can be de-convolved mathematically to analyze the areas under the waveforms if the. increased sensitivity of "matrix inversion" peak analysis is required. Thus emission dyes may sometimes offer increased sensitivity over absorption dyes. However, statistical requirements for the minimum number of spheres required for a 'significant' measured value in a given tissue sample (typically 400 spheres per-sample) partially offset the major advantage in the sensitivity with which fluorescent, as opposed to absorption, dyes may be detected. The primary advantage of fluorescent dyes appears to be their (i) excitation with a distinctive frequency of radiation in order to fluoresce, and (ii) their potentially sharper, or narrower 'peaks', both making it theoretically possible the use wider palettes of non-interfering colors than with purely absorption dyes.

When the (ii) introducing of the CM is into the circulating blood of a live animal, and when the (iii) determining is of the concentration of dye within the circulating blood, and when the (iv) recovering of the CM is from harvested animal tissue and blood by process of tissue and blood processing, then the (vi) measuring serves as a quantitative indication of the concentration of the dye in the harvested tissue and blood, and thus of the flow of the blood within which the CM, and the dye, were contained to the harvested tissue.

The (i) coloring is typically of each of several different types of microspheres: the microspheres of each type becoming labeled with an associated one of a plurality of different colors. The quantitative photometric spectrum of each color is both a) individually uniquely identifiable, and b) distinguishable from the photometric spectrum of all other colors. When the (ii) introducing, and the (iv) recovering, are of the several different types of microspheres—either of which steps may transpire separated in time and/or space, and may be repeated—then the (vi) measuring in a spectrophotometric procedure is of the composite quantitative photometric spectra of the several recovered dyes. Accordingly, an expanded method includes the additional step of (viii) mathematically analyzing, or de-convolving, the composite spectra to account for spectral overlap between the individual spectra of the several dyes at each of several specific wavelengths, namely the wavelengths of the individual peak absorption (or emission) of the several dyes. The mathematical analysis preferably transpires by one of several computerized mathematical processes, including matrix inversion. Each such individual spectrum is a quantitative indication of the concentration of the dye associated with each individual type of labeled CM, and a corresponding indication of the flow of that (those) fluids within which each type of CM was previously resident into the volume.

For emission spectrometry (as is taught in the predecessor patents) the (vi) measuring and (viii) analyzing steps are both easy and susceptible of automation. Despite their relative ease and simplicity, the steps are fully capable of accurately simultaneously determining the absolute, and relative, abundances of a number of different types of dye which are within a corresponding number of different types of CM. These different types of CM may be of different sizes, densities, shapes, or surface characteristics—each of which may have correspondingly different propensities to lodge within tissue or other material (such as soil) contained within the volume. The different types of CM may have been placed within several different flowing fluids that were subsequently mixed. The different types of CM may have been placed within the same stream of flowing fluid at different times. Accordingly, just one automated photometric analysis readily yields an abundance of temporal and spatial information regarding fluid(s) flow(s) and fluid mixing. Such abundant information is, in particular, eminently suitable for medical blood flow analysis including regional myocardial blood flow (RMBF) analysis, but is not so limited.

The methods of the predecessor patents were validated by its production of quantitative results that are. in close correlation to RMBF measured by 15 μm diameter radioactive microspheres after intracoronary injection in 4 pigs (r=0.98), and after intra-atrial injection in 4 dogs (r=0.97). The methods of the related predecessor patents are (i) fast, (ii)-easy, (iii) susceptible of automation and (iv) cost-effective, while avoiding all-problems related to radioactivity. However, tissue digestion is still required.

When referring to microspheres, radioactive microspheres and dye-colored microspheres are called "types". Each particular radioisotope, having a particular emission energies, that serves tc radio-label microspheres of the radioactively-labeled type (i.e., RM) is spoken of as creating a "species" of that type. Similarly, each different color of dye-colored microspheres, or CM, is spoken of as being a particular "species" of CM.

The present invention will later be seen to improve upon the very nature multiple-species type of microspheres, and to contemplate automatic accurate measuring of this new type of microspheres by neutron activation analysis, and without the necessity of digesting anything, or eluting the marker label from the microspheres.

2.4.6 The Desire and Need to Conduct Many Blood Flow Tests Simultaneously and/or in Series Sequence Before Subletting a Laboratory Animal to Euthanasia and Harvesting its Tissue When an expensive laboratory animal is subjected to blood flow analysis in order to evaluate the effects of various medical regimens, therapeutic and otherwise, there is a strong desire and need, based on efficiency of labor and reduction of cost, to accomplish as much investigation at one time as is feasible. A first injection of microspheres (of any type and species) typically later serves, when the animal's tissue is harvested, as a bench mark of normal blood circulation to the organ of interest, and serves as a baseline or reference point. After this bench mark injection the experimental protocol begins. For example, a coronary artery perfusing a portion of the heart of an animal might be partially or completely clamped, simulating a coronary event ("heart attack"). Another, second, injection of microspheres (of another type and/or species) generally serves to show, when later detected in harvested tissue, a diminished (or non-existent) blood flow, to the portion of the heart perfused by the clamped or partially clamped coronary artery. Other portions of the heart perfused by other coronary arteries will typically show no, or only slight, changes in blood flow during the same intervention. Similar injections at a number of subsequent times generally serves to define, when correlated with procedures and interventions performed on the animal and/or the administration of drugs to the animal, exactly how the animal's target organ is being perfused under several successive steps of an experimental protocol conducted over a period of time.

In order to extract from the selected harvested tissue, and from the blood samples, the record of the various blood flow circulations at the various times of the successive injections, it is necessary to separately evaluate the presence (or absence) of each different type and species of microspheres as were injected into the animal upon successive times. With radioactive microspheres, some 7–8 overlapping types of radioisotopes in common use each produce a distinct signature—permitting thereby an experimental protocol having up to 7–8 interventions and/or measurements at successive times. Of course, in accordance with the half lives of the radiolabels of the radioactive microspheres, the experimental protocol, regardless of the number of steps, should always be terminated, and the radioactivity analyzed before the shortest half-life isotope becomes too Weak to be useful.

Dye-labeled colored microspheres, or CM, are stable, and will support experimental protocols of long time duration. Presently, in the methods of the predecessor patents, typically more than five absorbance, and even more fluorescent, dye-colored microspheres may be commonly reliably separately distinguished in the presence of each other. The search goes on for palettes of even more dyes that are. individually distinguishable from one another in their spectrums of absorption or emission when a number:of such dyes are all mixed together.

In general, a desirable characteristic sought for dyes used to dye CM is a single very sharp peak absorbance or emission at a wavelength suitably displaced from all other dyes of the pallet. The spectrum of thousands of dyes have already been examined for these characteristics, and the search continues. However, with existing spectrometer sensitivities, and with analytical software programs of tractable size and execution times, which, most importantly, produce accurate quantitative results in the analysis of the individual spectral outputs of several different dyes (derived from species of CM) mixed together, it has, to date simply not been possible, to identify compatible dyes, and families of dyes, that number more than approximately one dozen. Accordingly, the number of separate steps in experimental protocols using CM is currently, circa 1993, limited to a dozen or less, and is more commonly and routinely (exotic dyes not being used), limited to about seven.

Researchers would prefer that the (i) duration of their experiments, and (ii) the number of intervention steps, in an experimental protocol should quite literally be unbounded. Although a total lack of limits may not be possible, it would be useful if some scheme could be developed to permit the individual detection in harvested tissue of large numbers (more than 15–20) of species of colored microspheres—which CM are not subject to deteriorate over time. Such detections would obviously permit that effective, extensive, multi-step experimental protocols could ensue over indefinitely long periods of time before it became necessary to perform euthanasia on the animal, and harvest its tissue, to evaluate the effect on blood flow of the step-wise procedure. Accordingly, blood flow experiments of considerable complexity, and many intervention steps, can be performed before the animal needs be subject to euthanasia, and its tissue harvested.

2.4.7 Efficiency Issues When Conducting Great Numbers of Blood Flow Measurements by Methods as are Taught in the Predecessor Patents The flow measurement methods taught within the related patents although a step forward over prior art radioactive microspheres and measurement methods—require certain steps that previous radioactivity-measuring methods using radioactive microspheres did not require. In previous radioactive methods; the abundance of radioactive microspheres (RM) in a unit sample of the harvested tissue is directly determinable by measurement of the level of gamma radiation emitted by each species of RM present within the sample. This measurement is performed without extracting the microspheres from the harvested tissue sample nor, for the matter, without extracting the radioactive substance from the RM.

When dye-colored microspheres (CM) are used instead, as is taught within the related predecessor patents, then a necessary and ultimate step is the quantitative assessment, by emission or absorbance spectroscopy, of the amount of dye that is within each species of the collective CM that are within the harvested tissue sample. This particular measurement step may be roughly as easily performed as are radioactivity measurements, and may be performed at roughly the same, or at lessor, cost than are radioactivity measurements.

However, in order to extract the dye(s) from the collective microspheres that are within the harvested tissue sample, certain additional process steps are required before the measurement step. First, the harvested tissue qroup must be digested. Next, the dye-colored microspheres (CM) must be recovered from the digestate, normally by centrifugation and filtration. Finally, the dye(s) must be eluted or dissolved from the recovered CM.

Of these three additional steps, the second is by far the most labor intensive, and is therefore the most expensive. Both the digestion of the tissue, and the eluting of the dye from the recovered CM are chemical processes requiring only the addition of appropriate reagents. The recovery of the CM by centrifugation or filtration is, however, a time-consuming and attention-demanding process that must be carefully performed.

Accordingly, it would be useful if some improvement could be made to the multi-step method of the related patents in order to (i) simplify and/or (ii) automate the. separation of the CM form the digestate, and/or the dye form the separated CM, or else (iii) eiimina e the requirement entirely. An improvement to CM would logically permit direct measurement of the CM that are within the harvested tissue sample in steps that were either (i) reduced in number, (ii) simplified, and/or (iii) automated, or semi-automated. Otherwise, a new type of microsphere is required, and that is the subject of the present invention.

SUMMARY OF THE INVENTION

The present invention contemplates (i) carrying on or within a carrier, particularly microspheres, (ii) certain chemicals, and more particularly certain stable isotopes of elements, that are detectable by neutron activation analysis. The preferred microsphere carriers carry the preferred stable isotopes into chemical admixtures or compounds, or insert the isotopes into or upon objects or devices, where the isotopes there after serve as markers or tracers that serve to permanently identify such admixtures, compounds, objects or devices.

This permanent identification continues after such change(s) and gross change(s) in form and/or in composition as may be occasioned by lapse of time, mechanical changes such as dissipation or wear or deterioration, or chemical changes such as oxidation or reduction or explosion. Basically, 1) the marking is as close to "forever" as anything yet known; and 2) the sensitivity of the tracing is as great as anything yet known, with the amount of tracers in the form of stable isotopes that are required for reliable detection being close to "infinitesimal".

As a further aspect of the present invention, the preferred microsphere carriers may be tailored to their environment, such as by being, most commonly, biodegradable. The biodegradability is not primarily so that the carrier microspheres may be removed from a biological environment at a time after they have served to deliver the preferred stable isotope(s) into that environment. Indeed, the microspheres will typically do no harm even should they persist forever: they will typically have no effect on the biological organism and they will never interfere with any subsequent detection and/or measurement of the isotopes by neutron activation analysis. Instead, the microsphere carriers are—in a manner totally unlike prior biological usages of microspheres as tracers where the microspheres were required to remain intact—preferably involved in, or even consumed by, some biological process(es) regarding which the condition(s), rate(s), and/or site(s) or such process(es) are of interest. An experimenter simply monitors the locations, and distributions, of the stable isotopes as an indication of what is happening to the microspheres. As a simple example, the carrier microspheres might be made of, or bound together by, some protein or sugar. When carried into the gut of an animal, these microspheres will persist intact for varying periods depending upon conditions. Observation and detection of the locations, and the time distribution, of stable isotopes within the gut of the animal—either as microsphere-sized agglomerations or as dissipated throughout some volume of the animals gut—clearly indicates what is happening to the protein or sugar microspheres within the animal's gut.

The concept of observing (by sensitive neutron activation analysis) the concentration and distribution of marker isotopes borne on microspheres where the microspheres themselves are not invariant, but are instead tailored to and/or interactive with their environment, is applicable to more than biological organisms. For example, microspheres carrying upon their surfaces a marine anti-fouling chemical agent, as well as (upon the surface, or within, the microspheres) certain marker isotopes, may be placed into a marine hull paint, imparting anti-algal or-other properties to the paint. Later analysis of samples from the environment in which a ship painted with such marine hull plate is docked will detect the marker isotopes with an extreme sensitivity that is much, much greater than any ability to directly detect the anti-fouling chemical. To such extent as the marker isotopes come to be found in the environment then the microspheres, and the anti-fouling chemical agent, may also assumed to be in the environment.

Thus a principle concept of the present invention is that a carrier, preferably microspheres, should carry a marker or tracer that is detectable by neutron activation analysis, preferably one or more stable isotopes, into a target and, occasionally, beyond.

1. The Carriage of Marker Elements Upon or Within Microspheres

The carriage of the chemicals, preferably certain stable isotopes of elements, upon or within the carriers, preferably microspheres, is important to the permanence of the marking.

In accordance with one of its aspects, the present invention contemplates separating (i) chemical markers for, and the chemical marking of, targets from (ii) the mechanical and/or chemical means by which the chemical markers are emplaced and retained on or within the targets. To repeat, the number of different admixtures; compounds, objects or devices in the world that may, as targets, desirably be marked, and particularly selectively marked, is vast. Meanwhile, the number of chemicals that may usefully serve as markers—and particularly certain stable isotopes of certain elements optimum for detection by neutron activation analysis in accordance with a separate aspect of the invention—is limited. It is hard, even impossible, to directly chemically or mechanically associate the limited number of marker chemicals (the stable isotopes of elements) with each of the vast number of different targets, thereby directly "marking" the targets. In accordance with the present invention, any requirement to chemically or mechanically "match" the (limited) markers to the (many) targets is obviated by the use of marker carriers: to wit, microspheres.

Not only do the microspheres carry (mechanically, or chemically, or both chemically and mechanically) the preferred marker(s), the carrier microspheres may readily be tailored (chemically, or mechanically, or both chemically and mechanically) to the intended applications environment. Once the "system" of any particular application is set in place, there is no need to ever separate 1) the microspheres from the marked target, nor 2) the marker chemical(s) (the stable isotopes of certain elements) from the microspheres. Indeed, this separation may be effectively impossible.

When and if the marked target or, more typically a minuscule portion or remnant thereof, ever comes to be assayed by neutron activation analysis which serves to detect the marker chemical(s) (the stable isotopes) that the target originally contained or attached (by dint of the incorporation or affixation of microspheres which themselves contain or affix the marker chemicals), then this assay, or analysis, will be performed on combined material of (i) the target, (ii) the microspheres and (iii) the chemical markers (the isotopes) in common, and all together.

This analysis of everything taken together and in gross presents no problem. The material of the target, and also the base material of the microspheres before association of the marker chemical(s), will not normally contain any appreciable amount of the marker chemicals, which marker chemicals are preferably stable isotopes of elements rare in nature, and are more preferably "rare earths". (Not all "rare earths" are truly rare, but most do not have wide distribution, occurring at but few and/or localized regions in the earth's crust.) Accordingly, substantially only those marker chemicals (those stable isotopes) that were originally added (via their microsphere carriers) to the target will be detected by neutron activation analysis.

This detection will transpire with exceedingly great sensitivity, meaning that a target may be indelibly permanently marked by but minute amounts of chemical markers (i.e., minute amounts of one or more stable isotopes of suitably rare elements, or at least elements that are uncommon within the target).

2. Markers Detectable by Neutron Activation Analysis

In accordance with another of its aspects, the present invention contemplates markers that are strongly reliably detectable, particularly in the presence of and commingled with biological material, by process of neutron activation analysis.

In accordance with the present invention, these (i) preferred chemical markers that are strongly (i) detectable, and (ii) reliably uniquely identifiable, in biological samples by process of neutron activation analysis consist essentially of stable isotopes of selected elements. With greater specificity, the preferred chemical markers meet the following criteria:

1) They are stable isotopes of certain elements selected in accordance with further criteria, next following.

2) For any given target and target sample, the proposed stable isotope(s) (if not also the element(s)) should be rare, and therefore all detection counts following neutron activation analysis can be attributed to presence of the marker element isotope(s).

3) Following neutron activation, the theoretical specific activity(ies) "s" of the marker-tracer-isotope(s) should be at least $1\times10^{10}$ disintegrations per minute per kilogram of marker-tracer-isotope(s). (This term "specific activity", or "s", will be seen to appear within the neutron activation equation later discussed in the DESCRIPTION OF THE PREFERRED EMBODIMENT section of this specification.)

Some of the factors that can contribute to this specific activity will be see; to be (i) a high natural fractional abundance (f), and (ii) a high neutron cross-section ($\sigma\approx10.0$ barns), as both of these terms appear in the. neutron activation equation later discussed in the DESCRIPTION OF THE PREFERRED EMBODIMENT section of this specification.

Although not absolutely necessary, following neutron activation, the daughter nuclide of the "ideal" marker-tracer-isotope will preferably emit only one primary photon having an energy greater than 100 keV with a yield of 100%.

Moreover, and again although not absolutely necessary, the half-life of the daughter nuclide ($t_{1/2}$) should be (i) at least two days, and more preferably greater than four days, but (ii) no longer than two years, and preferably no longer than one month; thereby (i) allowing shorter-lived background activity to decay before counting the sample, while at the same time (ii) not creating long-lived radioactive waste due to the marker-tracer itself.

There are a limited number of isotopes of elements in the periodic table that meet all these criteria, and all these preferences. Gold is one example. However, many isotopes—particularly those of the lanthanide family—partially meet most of these criteria and preferences, and can easily achieve the required specific activity. For example, an isotope with a low natural fractional abundance (f=1%) can still achieve the required specific activity following neutron activation if it possesses a higher neutron cross-section ($\sigma \approx 1000$) or if the isotope is enriched to achieve a fractional abundance approaching 100%. Overall, there are at least 25 isotopes of elements suitable for use as markers-tracers.

The use of stable isotopes of elements as marker-tracers essentially means that the marker-tracers are, short of atomic transmutation, indestructible. The elemental marker-tracers are forever detectable, and re-detectable—should an appropriately intense neutron flux, an appropriately prolonged decay counting period, and an appropriately sensitive radioactive decay event sensor be employed—at concentrations that are as small or smaller than those detectable by any other known analysis process. The sensitivity is thus down to the naturally occurring level of the marker-tracer in the sample.

Herein lies the relationship between the major aspects of the present invention. In accordance with the present invention, these (i) quite marvelous indestructible superbly-detectable unambiguously-identifiable marker-tracer elements are (ii) carried mechanically within (and more rarely, chemically upon) microspheres. The microspheres may be of selectively predetermined size (s), and selectively predetermined chemical composition and/or surface coating (ex of the marker-tracer isotopes), as is important in some biological experiments. The microspheres may be (further) chemically or (still further) mechanically combined with chemicals or other compounds that fixate the target of interest. For example, it is well known that the surfaces of microspheres may be coated with antigens to promote the selective uptake of the microspheres into certain tissues in biological experiments.

Accordingly, the present invention involves a method of (typically permanently) marking targets with stable isotopes of elements suitable for neutron activation analysis by act of carrying these stable isotopes within microspheres that are chemically and/or physically adopted to the targets. 3. Marking for Neutron Activation Analysis In greater detail, the marking of the present invention, which is normally permanent, is applied to diverse admixtures and/or compounds and/or devices. The marking is with chemical markers that are detectable by neutron activation analysis.

The present invention broadly satisfies the need for identifying objects or admixtures or compounds or the like for forensic purposes. "Marking" in accordance with the present invention transpires by the simple expedient of adding chemical markers in the form of one or more substances that are strongly detectable by neutron activation analysis to objects or to admixtures or to compounds, thus providing the objects or admixtures or compounds with a permanent "signature". The marking is normally at very low levels, and is inconsequential to the function (s.) of the objects or admritures or compounds. Once marked, the chemical markers cannot be (i) reasonably eliminated nor (ii) masked from detection by neutron activation analysis.

The chemical markers are preferably non-radioactive, stable, isotopes of selected elements. In accordance with the present invention, the admixtures or compounds or devices or the like are not marked directly with the stable isotopes but are instead marked by an intermediary carrier or carriers each bearing one or more stable isotopes. The marked intermediary carriers are, in particular and preferably: microspheres. The stable-isotope-marked microspheres are in turn used to mark (or to re-mark) something else, for example a biological sample.

in accordance with the fact that the detectable isotopes are stable, the marking and re-marking may transpire over time, in multiple steps, and/or at howsoever many indirect steps as are desired. For example, a single microsphere appropriately marked with plural stable isotopes, or, do encode for, by way of example, a unique identity (as may represent any of time, location, source, owner, intended deployment, etc. etc.) may be combined with, by way of example, an adhesive and applied to, by way of example, a security fence. In this example, animal fur or human clothing that is later determined by sampling and by (neutron activation) analysis to bear a pattern of traces of the selected isotopes may be assumed to have come into contact with the fence wheresoever, and at a later time then, the fence was marked.

As another example, batches of explosives may be individually uniquely marked directly by (i) microspheres containing multiple isotopes, and/or by (ii) selected combinations of single-marked microspheres. In this example, explosive residue that is later sampled and analyzed to show a pattern of some specific isotopes may be assumed to have originated in a batch of explosive so marked with these particular isotopes.

Isotope-marked microspheres are useful in biological investigation including, for example, flow measurement such as, in particular, the measurement of (i) regional organ blood flow and (ii) airway flow. Furthermore, isotope-marked microspheres are useful in drug delivery studies including (i) particulate distribution in drug delivery, (ii) immuinoassays, and (iii) high-throughput screening for drug discovery.

In one of its preferred embodiments as isotope-marked microspheres, the present invention presages a new generation of high-precision alternatives to traditional, radio-labeled life science products. The microspheres labeled with stable (non-radioactive) isotopes are used in an analogous fashion to their radioactive counterparts. However, the analysis of the tracer isotope(s) in samples of interest is performed by use of neutron activation technology. The biological marking system so based is highly sensitive, accurate and easy to use, providing in many cases information with improved sensitivity and specificity well beyond that achievable by colorometric markers and traditional radiolabels.

4. Chemicals (Stable Isotopes of Elements) Suitably Subjected to Neutron Activation Analysis as Makers, and the Detection of Marker Chemicals (Stable Isotopes of Elements) by Neutron Activation Analysis The preferred chemical markers of the present invention are typically permanent and without appreciable susceptibility to change within, or removal from, the compounds, objects or devices in which they become embedded, to which they become attached, or with which they become associated. If desired and even though microspheres may melt and, indeed, the marker isotopes themselves may turn into liquids or gases at sufficiently-high temperature(s)—it can usually be arranged that neither the microspheres nor the marker isotopes can be removed without causing such a change to the sample—such as melting—as is thereafter permanently unambiguously recognizable. Note that it is possible to, in certain cases, intentionally liberate the microspheres.

If necessary the. chemical marker, typically a stable isotope of an element, may be associated with a succession of one or more "marker carriers", and "carriers of marker carriers" which are most commonly in the physical form of microspheres, and layered microspheres. The microspheres, and microsphere layers, may have chemical properties targeted on the environment of use such as, by way of example, to (harmlessly, and at low numbers) chemically compound with the target, making subsequent removal while preserving the integrity of the target all but impossible.

Conversely, it should be understood that, where unauthorized removal of the markers is not an issue, as in biological experiments, then the marker (i.e., one or stable isotopes in or on a microsphere carrier) may intentionally be made inert, and non-reactive with the intended environment of use. The (typically microsphere-based) "marker carriers", and (the typically layered microsphere) "carriers of marker carriers", may be considered to be a "bridge" between the markers (the stable isotopes) and the intended environment of use.

Detection of the marker chemicals may transpire and re-transpire, at any time, and from time to time, and both before and after the occurrence of events, by subjecting and re-subjecting the chemicals, and any matrix in which they are then present or commingled, to neutron activation analysis. The neutron activation analysis is typically non-destructive to the compound, object or device within which the marker chemical is placed. Consider, by way of comparison, that neutron activation analysis has been deemed safe for use on all the diverse materials as. may be contained in luggage carried on airlines.

In accordance with the well-known principles and method of neutron activation analysis, the marker chemicals (and surrounding substances) are bombarded with neutrons so that atoms of these chemicals become excited to a higher energy level. The subsequent radioactive decay of these marker chemicals from their excited atomic states transpires over time as discrete events that nay readily be detected— essentially individually detected—by nuclear scintillation counters and like devices. The marker chemicals are accordingly detected essentially at the levels of individual atoms, and over a vast range of densities. Depending upon the radioactive half lives of the excited marker chemicals, and the amount of marker chemicals present in the sample being analyzed, analysis may typically take some hours or days or even longer. And analysis requires, of course, an intense neutron source, such as is normally associated with a research reactor. However, by the well-understood quantum mechanical principles of radioactive decay, quantitative measurement of the number of marker chemical molecules or atoms present may essentially be obtained, with sufficient time, to any desired degree of mathematical accuracy.

Notably, the marker chemicals may be detected by neutron activation analysis over a vast range of densities. A neutron a neutral particle. Therefore, neutron flux can effectively penetrate dense material. The resultant radioactive emission of the tracer is in the form of a photon. A photon is an energetic, massless particle that can be emitted from dense material of a reasonably sized sample (i.e., some few grams or tens of grams) with little self-attenuation. As a result, this technology can provide a detection method requiring minimal sample preparation and that can be used in a wide variety of applications.

The preferred marker chemicals are not common, let alone in combination. The marking thus has a superb "signal-to-noise": once an object, admixture or compound is marked then it can be, depending upon the density of the marking, detected indefinitely long at an indefinitely great dispersion.

Most typically in biological and in other applications of the materials and methods of the present invention there is at any one time but one potential "target" in the "field of view", and the only interest of the investigator is in (unambiguously) identifying this target and/or its abundance the sample. However, it should be understood that the present invention works to detect both (i) multiple targets, and (ii) strong targets in the presence of weak targets, occurring concurrently.

For example, consider that multiple marked targets should be, sometimes over a period of years, "loosed" upon the environment. Although such "marking" of multiple targets in the environment as may cumulatively occur over years and decades may be assumed to be innocuous as regards any environmental impact, some thought may usefully be applied as to just how to mark these multiple targets. For example, some tens of thousands of batches of explosives might be used coextensively in a single rock quarry over a period of decades. In the matter of how to uniquely encode, or mark, each of these batches both information theory, and industry standards and assigned usage, assume a greater role than it is common for, by way of comparison, bar codes. It is possible for a well-thought-out scheme to, by use of 25+ tracer-marker isotopes, uniquely identify each of many millions of targets each of which is differently marked, sometimes even while in the presence of other targets. In the example of the stone quarry, residues of the explosive(s) most recently used would be expected to be most pronounced in the newly shattered stone, with most stone that had been strongly marked by explosive blasts some years earlier having since been hauled away. It thus becomes possible in some situations, and by judicious planning, to detect individual targets even if other targets are concurrently present to a greatly reduced degree. All residual tracer-markers un-associated with the dominant target clearly constitute "noise" to the detection, and unique identification, of the dominant target.

The marker chemicals of the present invention are not destroyed nor permanently changed by being subjected to neutron activation analysis, and can be analyzed and re-analyzed. Neutron activation analysis is completely non-destructive of the marker chemicals analyzed. This characteristic supports that samples of marked compounds and devices preserved at, usually, tire of manufacture may be analyzed for their detail salient characteristics at any time in the future, and that unknown samples may likewise be analyzed and re-analyzed as may prove important, for example, in verifying and re-verifying their detail nature and their value as evidence in a judicial proceeding.

For example—and continuing with the example of explosives although any of oil, pollutants and art are equally valid—a minute sample of an original, marked, item or compound of, for example, a particular batch of an explosive may be preserved. If the explosive residue of a bomb site later analyzes to the particular chemical markers or series thereof that this heretofore untested sample is supposed to contain, then it is a simple and straightforward matter to test and re-test both reference and sample until all possible information is derived from both.

5. The Packaging and Use of Marker Chemicals Detectable by Neutron Activation Analysis, Including in Microspheres and Including for Use in Blood Flow Analysis The present invention contemplates that chemicals detectable by neutron activation analysis may be incorporated within microspheres, and that families of such chemicals may be used to lend unique identities to multiple microspheres, and families of microspheres.

As well as their obvious physical properties of size, weight, density, etc., the microspheres may have other chemical properties including, inter alia, a surface incorporation of antibodies or proteins. The microspheres so marked become lodged by the circulating blood within selected tissues of an animal during blood flow analysis experimentation. They may remain there, substantially imperviousness to alteration, indefinitely. If and when tissue containing the marked microspheres is ever harvested, it may be subjected to neutron activation analysis, normally in bulk and without any preparation whatsoever, so as to determine the absolute and relative abundances of; the microspheres, and each different type thereof, by measurement of the radioactive decay, which is at a different energy signature for each type of chemical marker as is associated with a corresponding type of microsphere.

Notably, the sample not only need not be purified or eluted or otherwise treated, but is substantially impervious to contamination, and need not even be isolated (save only from new marker chemicals). The sample may commonly be put in a closed noncontaminated vial or other container, and the entire vial subjected to neutron activation analysis. Containing no marker chemicals itself, the container vial has no influence on the measurement results.

Quick, easy and accurate measurement of blood flow to diverse tissues as is performed in blood flow analysis experimentation is thus obtainer: marked microspheres inserted into the bloodstream. of a live experimental animal are subsequently detectable in the harvested tissues of the animal by to such quantitative accuracies as are a indicative of the former flow of blood containing the microspheres to the tissues of the animal.

These any other aspects and attributes of the present invention will become increasingly clear upon reference to the following drawings and accompanying specification.

BRIEF DESCRIPTION OF THE DRAWINGS

FIG. 3 is a Table 1 providing the important physical characteristics of eight different isotopes that are suitable as labels for microspheres to measure regional perfusion.

DESCRIPTION OF THE PREFERRED EMBODIMENT

Figure 1:
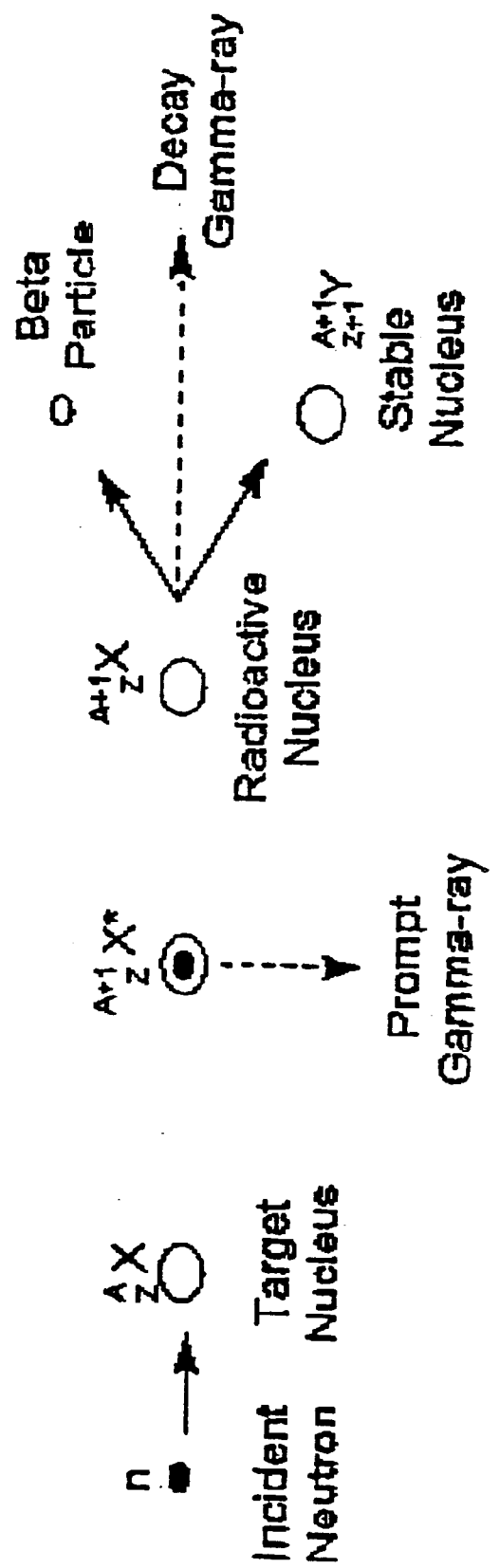
FIG. 1 is a prior art diagram of the principles of neutron activation analysis.
Figure 2:
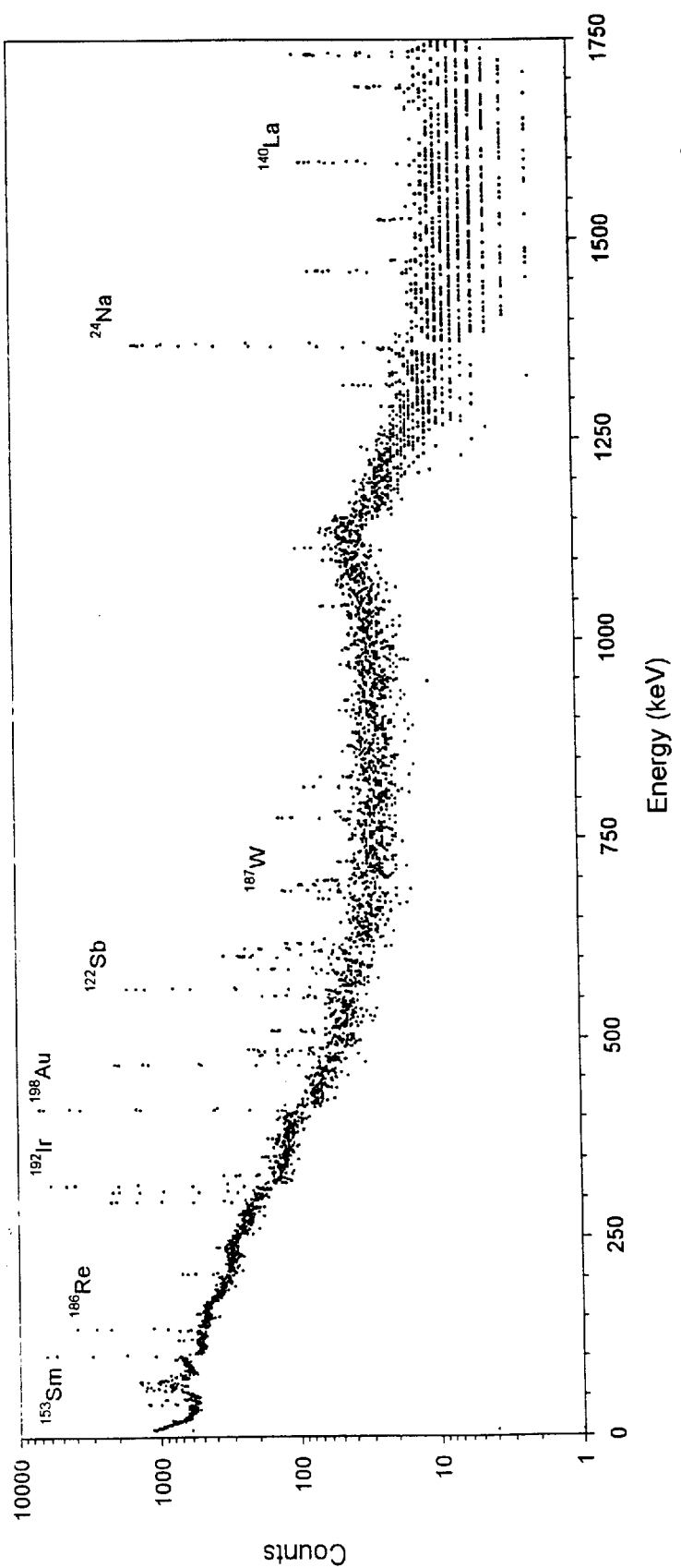
FIG. 2 is an emission spectra from a 5 g liver segment containing six labeled microspheres (samarium, rhenium, iridium, gold, antimony, and lanthanum); the spectra showing the presence of the tungsten monitor which is added to the sample vial to account for potential variations in the neutron flux and sodium which is the major contributor to background noise for most biological samples.

1. Non-Radioactive, Stable, Isotope-Labeled Microspheres 1.1 General Sequence of Making and Using Isotope-Labeled Microspheres In one of its aspects the present invention is expressed in non-radioactive, stable, isotope-labeled microspheres. Preferably some eight or more different, stable, isotopically-labeled microspheres are to be made available to experimenters.

It is intended that isotope-labeled microspheres shall typically come in 2 ml glass serum bottles containing approximately 5 million spheres. The microspheres are 15 $\mu$m in diameter and are suspended in normal saline containing 0.05% Tween 80 and 0.01% Thimerosal as a bacteriostat.

The tissue sample vials in which the tissue samples are to be placed are contaminant-free. The preferred sample vials are made from polypropylene, cleaned to remove trace contamination and calibrated for use in the particular activation and counting system of the assayist, which quite reasonably requires the use of its own microspheres and vials must be used for the assay.

The assayist typically charges a per-sample assay fee for the assay service. The results of the assay are normally reported as the total disintegration per minute (dpm) measured in each sample for each corresponding microsphere label. If preferred assayist BioPhysics Assay Laboratory, Inc., 280 Wellesley Avenue, Wellesley Hills, Mass. 02481 (Phone/Fax: (781) 239-0501) [BioPAL] is used, then the absolute blood flow (ml/min/g) measured in each sample can also be calculated for an additional assay fee.

1.2 Metallic Isotope Dye Preparation

Stable isotope labeled microspheres can be fabricated in a number of ways, but the first step is to make a solvent-soluble metallic complex of the desired stable isotope. Typically this can be done by first preparing a metallic AC-AC (acetylacetonate) solution using a method similar to that of Brown, et al., J. Organic Nuclear Chemistry, Vol. 13, pp. 119–124, 1960.

For example, Lanthanum AC-AC complex can made by dissolving 1.0 gm of a metallic salt lanthanum ($LaCl_3$), in 40 ml of de-ionized water using 0.1 normal hydrochloric acid (HCL) to effect. Next, blend the solution using a stirring plate and a stir bar while adjusting the pH to 5.0 using 0.2 normal sodium hydroxide. When the mixture is thoroughly mixed, stir in 10 ml of 2,4 pentanedione and allow the mixture to fully -homogenize (approximately 10 minutes). After the mixture is thoroughly homogenized, further neutralize the solution using sodium hydroxide until a stable pH of 6.5–7.0 is obtained.

The solution is then placed in a constant temperature bath at 65°–70° C., with no further agitation for one hour. After one hour, cool the solution down to room temperature (requiring approximately 1.5 hours).

Add 40 ml of benzene to the mixture and thoroughly homogenize by stirring for ten minutes. Transfer this mixture to a separating funnel and allow to stand until the metallic complex has floated to the top. Pour-off the liquid-phase and set aside for further processing. Transfer the metallic complex to a dish to air dry under a stream of 65° C. air. Add 20 ml of benzene to the recovered liquid phase from the separating funnel step. Recover any remaining metallic complex by again using the separating funnel and this material to the drying dish. Dispose of the liquid-phase after the second separation step. Store the dried metallic AC-AC material in a covered container at 0° C.

1.3 Fabricating Microspheres

Making of stable-isotope labeled polystyrene latex microspheres can be accomplished in one of several ways. Microspheres labeled with a stable-isotope metallic complex can be fabricated using a method similar to that described in "Neutron-Activated Holium-166-Poly (L-Lactic Acid) Microspheres: A Potential Agent for the Internal Radiation Therapy of Hepatic Tumors", J. Nuclear Medicine, R. J. Mumper, U. Y. Ryo, and M. Jay, Vol. 20 No. 11, 2139–2143, 1991.

Alternatively, commercially manufactured polystyrene latex microspheres can be 'dyed' using a solvent-solution of the stable-isotope metallic complex as described in the publication "Uniform Latex Particles", Seradyn Inc, Indianapolis Ind., 46206, author Dr. Leigh Bangs. Microspheres suitable for dyeing are available from Bangs Laboratories, Fishers Ind.

In addition, stable isotope labeled microspheres can be fabricated by covalent or non-covalent coating of the outside surface of the microspheres with the metallic complex in a manner similar to the NEN-Trac® radioactive microspheres manufactured by New England Nuclear, Boston Mass. 02118-2512. (NEN-Trac® is a trademark of New England Nuclear.)

For example, lanthanum labeled polystyrene microspheres can be fabricated by first making a 3% solution of polyvinyl alcohol (PVA). This is done by adding 2.4 g of polyvinyl alcohol to 800 ml of de-ionized-water in a 1-liter beaker. Place the beaker on a stir plate and put a stir bar in the beaker. Cover the top of the beaker with plastic wrap to prevent evaporation and set the stirring to a fairly rapid rotation rate. Allow the mixture to stir until thoroughly emulsified which will take overnight. Keep the mixture covered and at room temperature.

The microspheres are fabricated by adding the components together with constant stirring under a nitrogen gas environment. This can be accomplished by fabricating a mixing-box that can be sealed and purged with nitrogen gas. The mixing box has provisions for an external stirring system to stir the vinyl solution continuously while the microspheres are forming. The box is continuously purged with a low flow of nitrogen during the first hour of processing.

Dissolve 2 g of polystyrene material in 30 ml of chloroform in a 50 ml glass beaker. It will take about one hour for the polystyrene to dissolve, vortexing or agitation will speed the process.

Measure out 0.5 g of the previously fabricated metallic AC-AC complex and place in a small beaker inside the mixing box. Pour 300 ml of the PVA solution into a 500 ml glass beaker, then place the beaker in the mixing box. Thirdly, place the beaker of chloroform/vinyl in the mixing chamber. Seal the mixing box and purge the box with nitrogen. Begin stirring the PVA solution in the 500 ml beaker at 1000 rpm. Using a glass syringe and a tube through the mixing-box side, transfer the metallic complex (lanthanum AC-AC, in this example) to the chloroform/vinyl solution and allow the mixture to fully dissolve. Slowly add the metallic complex plus chloroform/vinyl solution to the stirring PVA (1000 rpm). Allow this mixture to stir for a minimum of one hour under 1.5 the nitrogen atmosphere, and afterwards continue stirring for an additional 12 hours in air inside a fume hood. This additional time is to insure that all the chloroform ha-s evaporated away.

The microspheres are next washed and sorted by size. Washing is accomplished by re-suspending the microspheres in a 1-liter beaker containing solution of de-ionized water with 0.05% Tween 80 as a surfactant. Place the beaker on a stir plate, place a stir bar in the beaker and stir the mixture at a medium rate. Place the tip of an ultrasonic homogenizer ("sonicator") in the beaker and sonicate the microsphere mixture at low power for 5 minutes while stirring. Transfer the microsphere mixture to multiple 50 ml centrifuge tubes and centrifuge the tubes for 10 minutes at 1500 g (2500 rpm on most bench-top centrifuges).

Aspirate the supernate down to a safe level above the microspheres and re-suspend with 30 ml of 0.1 normal hydrochloric acid (HCL) to remove any unincorporated metallic complex from the outside surface of the microspheres. Sonicate each of the 50 ml tubes for 30 seconds and then fill each tube to the top with the HCL solution. Centrifuge the tubes again for 10 minutes at 1500 rpm, aspirate the acid solution. Re-suspend the microspheres in water plus 0.05% Tween 80, vortex mix, centrifuge, aspirate down to the microsphere pellet. Repeat the last step three times to remove any remaining acid. After the last wash step do not aspirate but instead combine the microspheres from all the tubes into a clean 1-liter glass beaker. The microspheres can now be sized using a mechanical microsiever (Gilson Company,Inc, Worthington Ohio Model SS-5 or equivalent). For the measurement of blood flow in most species, microspheres of 10 to 15 $\mu$m in diameter have been found to be optimal.

The sized microspheres are washed in alcohol, centrifuged and the supernate aspirated away, after which they are allowed to air-dry overnight. The dried microspheres are then re-suspended in an injectable saline solution containing 0.05% Tween. 80 at a concentration of 2.5 million microspheres per milliliter. The Tween 80 is a surfactant that is used to minimize aggregation of the microspheres in solution. If the microspheres are going to be stored for later use, 0.01%. Thimerosal should be added to the solution as a bacteriostat.

1.4 Characteristic Uses of Isotope-labeled Microspheres so Produced

Stable isotope-labeled microspheres so produced have a wide variety of potential applications, most- notably to the life science community is its use in regional blood perfusion and particle deposition studies. Normally at least eight different isotopic labels, at a minimum, can be simultaneously assayed by neutron activation. Investigators use the stable isotope-labeled microspheres in an analogous fashion to their radioactive and dye-elution-based (colorometric) counterparts, the major difference being that samples of interest are subsequently sent to BioPAL for analysis of their tracer(s) content, with the results of the assay typically being returned to the customer within a week. The standard report sheet of BioPAL provide the customer with the number of disintegrations per minute (dpm) measured for each labeled set of microspheres, which is analogous to the traditional radioactive method. Given additional information provided by the customer, BioPAL can also calculate the blood flow (ml/min/g) for each tissue sample.

The stable isotope-labeled microsphere product and service typically offers a cost-savings of from 50–200% depending on the method being compared, improved sensitivity (with one microsphere resolution), re-assay and archiving ability, and the elimination of the risk of sample contamination and lose associated with other nonradioactive methods.

2. Details of the Assay of the Isotone-Containing Microspheres

2.1 Mathematical Basis of Neutron Activation Analysis

Assays in accordance with the present invention are based on neutron activation analysis, typically as performed by a service provider (i.e., someone other than the experimenter and user of the labeled microspheres). The preferred assayist/analyst—said BioPAL—employs customized neutron activation protocols for the measurement of trace and ultra-trace elements.

Neutron activation analysis to measure the concentration of stable isotope-labeled microspheres is a two step process. The first step requires exposing the sample to a high neutron field sufficient to generate a strong radiation signal from each isotope label.

The general principle underlying neutron activation is that an incident neutron is captured by an atom forming a radioactive daughter nucleus. The number of radioactive emissions is directly proportional to the mass of the parent isotope. See the diagram of FIG. 1.

In practice, a sample is exposed to a flux of neutrons, $\phi$, for a given time, t. The specific activity, s, induced in any parent nuclide can be calculated from the formula:

$$s = 6.02 \times 10^{26} \phi \sigma f A^{-} (0.5)^{t^1/t_{1/2}} [1-(0.5)^{t/t_{1/2}}]$$

where: s=specific activity in disintegrations per unit mass ($s^{-1} kg^{-1}$), $\phi$=flux of neutrons ($m^{-2} s^{-1}$), $\sigma$=cross-section for neutron interaction with the parent nuclide (in barns, or $m^2$), f=fractional abundance of the parent nuclide, A=atomic weight of the parent element, $t^1$=time between activation and counting (hours), t=activation period (hours), and $t^{1/2}$=half-life of daughter nuclide (hours).

In accordance with the present invention, a marker will be marked with an isotope that following neutron activation will generate a theoretical specific activity (s) of which exceeds $1 \times 10^{10}$ disintegrations per minute per kilogram of tracer, as appears in the above equation for specific activity, induced in many parent nuclide during neutron activation.

2.2 Qualities of Preferred Isotopes, and the Preferred Isotopes of the Present Invention for Use as Markers Suitably Assayed by Neutron Activation Analysis The neutron activation process of the present invention will preferably activate most. preferably all, individual members of most, preferably all, species of isotopes present in the sample. Therefore, an "ideal" stable isotope for use as a tracer in biological and other studies would have the following characteristics (as previously discussed in the SUMMARY OF THE INVENTION section of this specification) in order to be most effectively measured against background noise:

1) The marker element has a stable isotope.

2) For any given sample, the proposed stable isotope should be rare, and therefore all detection counts during neutron activation analysis can be attributed to presence of the tracer.

3) The fractional abundance of the isotope (f) should be 100%. (See the term "fractional abundance" in the neutron activation equation of section 2.1, above.)

4) The isotope should have a high neutron cross-section ($\sigma$>100 barns) ("barns" have the unit of $m^2$). (See the term "$\sigma$" in the neutron activation equation of section 2.1, above.)

5) Following neutron activation, the daughter nuclide should emit a primary photon having an energy greater than 100 keV with a yield of 100%.

6) Because of their unique energy signatures upon decay from an excited state, the daughter nuclide must be, and innately will be, individually distinguishable from one another.

7) The half-life of the daughter nuclide ($t_{1/2}$) should be (i) at least two days, and more preferably greater than 4 days, but (ii) no longer than 1 year, and more preferably no longer than 1 month; thereby (i) allowing shorter-lived background activity to decay before counting the sample, while at the same time (ii) not creating long-lived radioactive waste. due to the tracer itself.

Also as previously discussed in the SUMMARY OF THE INVENTION section of this specification, only Gold (Au) substantially meets all these criteria. Other tracer elements must be selected in accordance with their ability to substantially meet, to a greater or a lessor extent, most criteria.

In choosing an appropriate tracer, consider that, for biological samples, sodium, potassium and chloride provide the greatest contribution to the background signal given their short activated half-lives ($^{24}$Na $t_{1/2}$=15h, $^{42}$K $t_{1/2}$12h, $^{38}$Cl $t_{1/2}$=37m) Compared to an ideal tracer, this background activity is low following the three-day decay period without having a significant loss in signal from the activated tracer. Moreover, following a five week decay period, most biological samples plus the ideal tracer content would be covered under Nuclear Regulatory Commission regulations for exempt concentrations (10 C.F.R. §32.11), and therefore can be returned to the researcher including a researcher at a non-NRC licensed laboratory.

There are a number of isotopes, particularly isotopes in the lanthanide family, that largely meet the characteristics of an ideal tracer.

One such isotope is gold, having a fractional abundance of 100% ($^{197}$Au) and a cross-section of 98.7 barns. The daughter nuclide of gold ($^{198}$Au) emits seven photons, one of which has an energy of 411 keV and a yield of 95.5%, while the other six photons all yield below 2%. The half-life of $^{198}$Au is 2.69 days.

Other usable isotopes include, but are not limited to, stable isotopes of antimony, lanthanum, samarium, europium, terbium, holmium, ytterbium, lutetium, hafnium, tantalum, tungsten, rhenium, osmium, iridium, scandium, bromide and still others.

2.3 Performance of Neutron Activation Analysis on Samples Containing Isotope-Labeled Microspheres in Accordance with the Present Invention Accordingly, an ideal isotope for use as a microsphere label will form a radioactive nucleus that would be short-lived and emit a gamma-ray during the decay process. The energy of the gamma-ray is discrete and distinct for each stable isotope. In general, samples will require an exposure of $1.0 \times 10^{20}$ neutron $m^{-2}$ to generate a useful signal. As a result, mid-size research reactors that can generate a neutron flux in the range of $10^{17}$ to $10^{19}$ neutrons $m^{-2}$ $s^{-1}$ and will provide the best source of neutrons. Other sources, such as sealed tube generators and accelerators, cannot currently achieve the necessary neutron flux or require too much energy and are therefore not cost effective. Research reactors have the added advantage of being able to generate a wide neutron flux beam suitable for activating large numbers of samples simultaneously.

Several methods can be used to introduce samples to the neutron field, such as robotic belts and pneumatic delivery systems. For example, a well-designed pneumatic delivery system can activate on average 4,000 samples per day. Most mid-size research reactor would be able to accommodate as many as 10 systems operating independently, thereby providing a daily theoretical throughput of 40,000 samples.

The second step is effectively measuring the emissions-of-interest following neutron activation. In addition to the stable isotope labels, the activation process will also activate other isotopes present in the sample adding background noise to the signal, thereby potentially decreasing the sensitivity of the assay. Given their relative high concentration in biological samples, sodium and chloride pose the greatest concern. However, given their short activated half-lives ($^{24}$Na $t_{1/2}$=15 h, $^{38}$Cl $t_{1/2}$=37 m) compared to the microsphere labels ($t_{1/2}$=2 to 100 d), this background activity will be low following a 2–3 day decay period.

It is also important to note that desalting methods exist and can be adapted to help remove NaCl and other contaminates from samples-of-interest. However, in most cases this step is not needed. Following neutron activation, samples are then stored in a secured, NRC-licensed, area for the decay of short-lived background activity.

Specialized, high-resolution detection equipment can than be used to identify and measure emitted gamma-rays. The number of emitted gamma-rays is directly proportional to the total mass of the parent isotope, and therefore is proportional. to the total concentration of the labeled microspheres contained in the sample. The sensitivity and specificity of a radiation detection system is dependant on many factors including background interference, intrinsic efficiency of the detector, source-detector geometry, sample size, and the times for irradiation, decay, and counting. The complexity of adjusting these variables is intensified when trying to optimize the system for multiple elements-of-interest simultaneously. Because quantitative gamma-ray spectrometry of low energy photons can be complicated by scattered electrons, resulting from higher energy photons generating background counts due to Compton scatter. Specifically, a photon entering a detector has a high probability of interacting with an electron. A fraction of the photon's energy is given to the electron, while the photon recoils with the remaining energy. This phenomena is called Compton scatter. Short ranged Compton electrons will deposit their energy within the detector and are represented as counts. These counts can confound the quantitative assessment of a complex gamma spectrum, such as those generated following neutron activation of a biological sample. Several methods can be used to reduce Compton contributions. One such method uses a Compton suppression system consisting of a large crystal ring detector surrounding a primary, high resolution detector. As the recoiled photon exits the primary detector, it has an opportunity to deposit its energy with the second ring detector. Deposition of the Compton electron within the primary detector should occur simultaneously with the absorption of the recoiled photon within. the ring detector. Operating the two detectors in anti-coincidence can reduce the Compton counts by a factor of 10, while the loss of counts in the total energy peak will reduced by less than 0.05%. Given recent improvement is detector technology and computer electronics, such a system can be designed and automated to process up to 1,000 to 2,000 samples per day. Having several systems working in series, such a counting system can easily handle the output of activated samples.

So functioning, the aforementioned BioPAL, in particular, offers the biomedical research and industrial communities access to the power of neutron activation technology for the measurement of trace elements. Using their isotope-labeled microspheres of their own distribution (manufactured by Triton Technology, Inc. in San Diego, Calif., in accordance with the one of the method taught above), the energy of the gamma-ray is discrete and distinct for each stable isotope. Specialized, high-resolution detection equipment is then used to identify and measure the emitted gamma-ray. The number of emitted gamma-rays is directly proportional to the total mass of the parent isotope.

The sensitivity of any nuclear reaction can be estimated using Equation 1. For Samarium, the potential reaction is $^{152}$Sm(n,γ)$^{153}$Sm; $t^{1/2}$=1.93 days. Therefore, using a flux of $8.0\times10^{16}$ (m$^{-2}$s$^{-1}$) and an irradiation time of 10 minutes, followed by a decay time of 2 days, a specific activity of $2.1\times10^{12}$ disintegrations per second per kilogram is obtained for $^{153}$Sm.

Therefore, this technique BioPAL (or anyone following the teaching of this specification) can determine less than $10^{-12}$ kg (1 ng) of Samarium using standard counting equipment. Given recent improvements in detector technology and computer electronics, this sensitivity can be at minimum improved by an order-of-magnitude.

2.4 Summary of the Intertwining of Neutron Activation Analysis and the Present Invention, with Particular Emphasis on Support for Biological Assays Neutron activation analysis is well known for its excellent sensitivity and elemental specificity for the simultaneous measurement of trace elements. See Anal Chim Acta 165, 1 (1984); Anal Chem 63, 1143 (1991); and Anal Chem 65, 1506 (1993).

Unlike other methods, such as atomic absorption spectrophotometry, neutron activation is not chemically or physically destructive. Therefore, samples can be re-assayed or undergo other chemical analyses following neutron activation. Neutrons are highly penetrating, therefore this method can be used to assay samples having a wide range of material compositions and densities. In addition, this assay can be structured so that it is completely self-contained, thereby minimizing the possibility of sample contamination and sample loss. Despite these advantages, this technology is not widely used because of limited availability of neutron sources, traditionally high activation costs, and long experimental turn-around times.

A major focus on applications of the present invention has thus been on the development of a new generation of high-precision alternatives to traditional, radioactive life science products. The preferred marked microspheres labeled with stable isotopes are used in an analogous fashion to their radiactive counterparts. The assay of the stable tracer(s) in samples of interest is performed by an analyst agent—an assayist—that is located at a source of neutron flux (normally a research reactor), and that performs the assays using neutron activation technology for a fee. This method of local experimentation coupled with a remote, service-bureau-provided assay, has been found to be both accurate and easy to use.

In many cases, this approach provides information with improved sensitivity well beyond that achievable by colorometric markers and traditional radiolabels. Given the economies of scale resultant from the large number of samples that the assayist analyzes daily, the assay may be competitively priced with what it would cost an investigator to do his or her own analysis based on an alternative, prior art, marking system. The assay can usually be customized, supporting where relevant computations based in the quantitative measurement of trace elements in various material compositions. For example, when the assayist understands that it he assaying a harvested tissue for a sequence of A, B, C, D marked microspheres as are indicative of blood flow to the tissue at time $T_1$, $T_2$, $T_3$, $T_4$ in a blood flow analysis experiment, then he may well report the results as (relative) blood flow, as well as the qualitative levels of abundance.

3. Advantages of the Present Invention

The core technology of the present invention is neutron activation analysis. Neutron activation analysis is well known for its excellent sensitivity and elemental specificity for the simultaneous measurement of trace elements. Stable-labled research products in the form of chemicals suitable to neutron activation analysis, with an accompanying vender neutron activation analysis service, offers the life science community the following advantages:

The use of radioactive and hazardous reagents may be totally avoided. The assay of the present invention is non-radioactive for the researcher while requiring none of the hazardous reagents associated with colorometric measurements. Therefore, researchers and biotechnology companies do not require an Nuclear Regulatory Commission (or equivalent foreign regulatory authority) license nor will they need to purchase and maintain expensive in-house laboratory equipment.

The present invention accords even the most modest research activity full access to a highly sensitive and specific assay technology. Namely, neutron activation provides a highly sensitive measurement of the stable-labeled products in accordance with the present invention. Unlike other methods, assay in accordance with the present invention does not require extensive sample preparations that can result in sample contamination or sample loss. In many cases, (i) the stable-labeled products subsequently subjected to (ii) an assay service, both in accordance with the present invention, offers increased, sensitivity well beyond that achievable by colorometric markers and traditional radiolabels.

The present invention accords multiple labels. Nature has provided a reasonably large number of stable isotopes that can potentially be used—some more effectively than others—to label research products and can be efficiently and simultaneously assayed by neutron activation.

The present invention offers flexibility to researchers when developing experimental protocols. In addition to easily permitting multiple labels, neutron activation is not chemically or physically destructive. Therefore, samples can undergo other chemical analyses following the assay.

The present invention permits that the original sample should be archived, and re-assayed if, as and when desired. Assayed samples can be stored for future reference and re-assayed, if necessary, at a later date. Furthermore, samples can be re-assayed to provide additional signal amplification retrieving information that would otherwise be lost using alternative technology.

The present invention accords reduced experimental start-up costs. Researchers and research institutions do not have to learn a new technology, nor invest in expensive hardware, nor purchase high-priced reagents, nor secure additional laboratory labor for the performance of assays in accordance with the present invention.

The present invention readily permits the evaluation of highly concentrated or dense samples. Neutrons are highly penetrating. Therefore, highly concentrated samples or samples of varying material compositions such as bone or teeth can readily be assayed. This assay, therefore, eliminates signal quenching errors associated with both beta-radiation counting (i.e. 3H, 14C, 32P, 35S) and optical measurements.

4. Non-Radioactive Stable Isotope-Labeled Microspheres for Physioloqical Studies Non-radioactive, stable, isotope-labeled microspheres in accordance with the present invention provide the biological research community with a cost-effective alternative to the use of radioactive, and or colorometric (dyed) microspheres for the measurement of regional organ blood flow and particle deposition studies.

The experimental method for using stable-labeled microspheres is identical to the traditional radioactive method. See Prog Cardiovasc Dis 20, 55 (1977); and Basic Res Cardiol 80, 417 (1985). The method of the present invention differs only in the assay of the microspheres is performed at the location of a neutron source, normally a research reactor, normally by a provider of neutron activation analysis assay services such as said BioPhysics Assay Laboratory, Inc., 280 Wellesley Avenue, Wellesley Hills, Mass. 02481 (Phone/Fax: (781) 239-0501) ["BioPAL"] [the "assayist"].

At the close of the experiment, tissue samples of interest are collected, weighed and sealed in tracer-free polypropylene sample vials. If blood flow measurements are to be calculated (ml/min/g), then blood samples are sent to the assayist for analysis, who uses neutron activation technology for the measurement of microsphere content. The researcher can typically expect the results of the assay within seven working days via e-mail.

The assay procedure of the assayist is not chemically or physically destructive and the measurement can be repeated and re-repeated on the samples or any of them at a later time. See, for example, Anal Chim Acta 165, 1 (1984). Therefore, samples may be returned to the researcher for other analysis or archived for future reference. The ability to re-assay stored samples is a major advantage for pharmaceutical companies in meeting FDA/GLP requirements.

5. Non-radioactive Immunochemical Assay Kits

The present invention is embodied in non-radioactive immunochemical assay kits supportive of the non-radioactive methods of the present invention in immunochemical applications. In this case the microspheres are coated or impregnated with biological substances, for example monoclonal antibodies, as well as the stable isotopes that serve as tracers/markers.

The inventors of the present invention are actively developing, circa 1999, new products adapting neutron activation technology to measure stable, isotopically labeled monoclonal antibodies (r other biologically active compounds) for use in immunochemical applications. This technology will allow for the simultaneous evaluation of multiple-labeled monoclonal antibodies (greater than two) in a single sample and should prove to be more cost effective then current fluorescent activated cell sorting technology. Neutron activation is not chemically or physically destructive and the measurement can be repeated. See Anal Chim Acta 165, 1 (1984). Therefore, samples may be returned to the researcher for other analysis or archived for future reference. This ability to re-assay the same sample will provide a major advantage for pharmaceutical development. Preliminary findings suggest that this technology will also provide improved sensitivity well beyond that achievable by current fluorescent markers and the traditional radioimmunoassays.

6. High-Throughput Screening for Drug Discovery

The present invention supports and permits customized high-throughput screening for drug discovery and evaluation.

Neutron activation analysis provides the researcher with capabilities not readily available with other assay technologies. For example, neutron activation analysis can sensitively and accurately measure several (ultimately ten or more) stable isotope labels, simultaneously. This offers the potential of being able to measure multiple assays in a single well. Screens designed to look for functional relationships among related molecules are also possible within a single well.

Because neutron activation is nondestructive to the sample, small peaks found in the first pass can be reactivated for longer times to increase assay sensitivity. This variable sensitivity feature of neutron activation may be able to detect hits that might be missed by other technologies.

After the initial measurement, samples can be archived for long periods of time. Since the labels are atomic elements they will not break down. If it becomes important to re-assay a sample(s) at a later date (months to years later), this is possible.

Neutrons can penetrate solid tissues, so multi-label screening of intact tissue derived from in vivo models is possible.

The above features of neutron activation can potentially speed up throughput by a factor of at least ten, lower costs, allow for "smarter" assay designs, do direct in vivo assays and save time.

7. Microspheres Tailored to, and Interactive with, the Environment into which they Transport the Marker Isotopes Microspheres in accordance with the present invention are most commonly inert, and stable, in the environment into which they transports and deliver the marker isotopes. They may be, however, made tailored to, and intentionally interactive with, this. This interaction is normally over a longer time, or in the face of later-arising conditions, than necessary to transport the marker isotopes into the environment of interest.

The tailored microsphere carriers are most commonly biodegradable. This biodegradability is not directed to eliminating the microspheres from a biological environment at a time after they have served to deliver the preferred stable isotope(s) into that environment. Instead, the reaction of the microsphere carrier with the biological environment—so as to degrade, or whatever—is important as an indication of the time(s) and location(s) of biological reactions not between the environment and what the microspheres carry, but between the environment and what the microspheres themselves are. This is totally unlike the prior biological usages of microspheres as tracers where the microspheres were required to remain intact. The tailored microspheres are involved in, or even consumed by, some biological process(es). The reason that this is of interest is that the condition(s), rate(s), and/or site(s) or these biological process(es) may be determined by monitoring over time the locations, and distributions, of the stable isotopes as an indication of what is happening to the mlcrospheres.

As a simple example, the carrier microspheres may be made of sugar, much like a confectioner's hard shell candy coating, or of a protein, for example casein (from milk). When carried into the gut of an animal, these microspheres will persist intact for varying periods depending upon conditions. Observation and detection of the locations, and the time distribution, of stable isotopes within the gut of the animal—either as microsphere-sized agglomerations or as dissipated throughout some volume of the animal's gut—clearly indicates what is happening to the protein or sugar microspheres within the animal's gut. For example, the digestion of sugar microspheres may differ in animals (including people) having stomachs that are relatively more or less acidic. And casein is involved, or course, in lactose intolerance which manifest as the total or partial inability of some people to digest this protein.

This concept is broad: microspheres may be made to be tailored to and/or interactive with their environment for any legitimate reason. For example, microspheres can carry specific materials regarding which dissemination and distribution of which in the environment, sometimes over a period of years, is desired to be studied, and known. The same microspheres will, in accordance with the present invention, also carry marker isotopes. The microspheres need not, and most often do not, bio-degrade. However, as they move in the environment so also do the carried isotopes move. These isotopes can be detected by neutron activation analysis with much, much greater sensitivity, and accuracy, than the specific materials. Where the microspheres are so also are the specific materials. Accordingly, detection and abundance measurement of the microspheres is equivalent to the detection and abundance measurement of the specified materials.

8. Use of the Nonradioactive, Stable-Isotope-Labeled, Microspheres of the Present Invention in Blood Flow Analysis As the above sections make clear, non-radioactive, stable-isotope-labeled, microspheres in accordance with the present invention have many uses. The microspheres are, however, of exemplary usefulness in blood flow analysis, and, accordingly, their use in this application is explained in detail.

8.1 Introduction to the Use of Microsnheres for Blood Flow Determination

Radioactively labeled polystyrene microspheres have been used to measure regional blood flow since the technique was first described in the late 1960's. See Circ Res 21, 163 (1967); Circ Res 23, 623 (1968); Circ Res 25, 581 (1969); and J Appl Physiol 31, 598 (1971). A review of the technique has been published by Heymann and co-workers. See Prog Cardiovasc Disease 20, 55 (1977)

Recently, nonradioactive colored have been used. See Circulation 78, 428 (1988); and Circulation 83, 874 (1991). Additionally, fluorescent microspheres have been used in these experiments. See Am J Pathol 103, 292 (1981); Kidney Intl 20, 230 (1981); Am J Physiol 251, H863 (1986); J Autonomic Nerv Syst 30, 159 (1990); and Am J Physiol 262, H68 (1992).

Previous techniques have called for the recovery of not only the microspheres, but also the absorbance/fluorescent dyes that the microspheres contain, from harvested tissue samples of animals, allowing blood flow quantification to be performed using instrumentation such as spectrofluorometers or fluorescence spectophotometers.

For example blood flow measurements using the Dye-Trak™ microspheres product of Triton Technology, Inc., San Diego have been validated in side-by-side comparisons with radioactively labeled microspheres. (Dye-Trak™ is a trademark of Triton Technology, Inc.). See the aforementioned Kowalik, et al. "Measurement of Regional Myocardial blood Flow With Multiple Colored Microspheres", Circulation, Vol. 83, No. 3, March, 1991. The two techniques exhibited equivalent maximum detection sensitivity and the correlation between flow measurements was excellent. The Dye-Trak™ microspheres are presently available in more than five colors, allowing effects of multiple physiological variables to be studied in the course of a single experiment.

The present invention has been seen to negate the steps of digesting the sample, recovering the microspheres, and eluting the absorbance or fluorescence dye from the recovered microspheres. Nonetheless that no dye is extracted from (recovered) stable-isotope-labeled microspheres in accordance with the present invention, the same (i) detection sensitivity and (ii) accurate correlation between flow measurements as with colorometric microspheres is enjoyed. This is because the present invention teaches a way to accurately quantitatively measure the amount of the marker element that is within the microspheres (and thus, indirectly, the abundance of the microspheres themselves) while this element is still (effectively permanently) within the microspheres.

Note that not only that the number, but the rate, of decay counts can be, and commonly is, measured.

8.2 Stable-isotope-labeled Microspheres

The microspheres of the present invention, as are their predecessor products, are uniform polystyrene microspheres with nominal diameters of 10 μm or 15 μm. They are commonly supplied as suspensions in 10 mL of 0.15 M NaCl with 0.05% Tweens$^{SM}$ 80 and 0.01% thimerosal. These 0.2% suspensions contain either $3.6 \times 10^6$ microspheres (10 μm diameter) per mL or $2.5 \times 10^6$ microspheres (15 μm diameter) per mL. The microspheres or each reagent contain a single marker element having a stable isotope. The decay energy(ies) of the excited form(s) of this element is (are) well resolved from corresponding decay energies of the excited form(s) of all of the other marker elements. The microspheres have a relative density of 1.05 g/mL, which is close to that of red blood cells (1.10 g/mL).

8.3 Uniformity of Stable-isotope-labeled Microspheres

The size uniformity of the microspheres determined by a suitable analytical method for determining particle size distribution. Each lot complies with the following specifications:

| Microsphere Diameters | Standard Deviation |
|---|---|
| 9.5–10.5 μm | <.45 micron |
| 15.0–16.0 μm | <.45 micron |

The actual measured diameter for each lot of microspheres is commonly printed on the product label.

8.4 Stability of Stable-isotope-labeled Microspheres

The stability of the stable-isotope-labeled microspheres is excellent in both dry and aqueous environments. Only a powerful organic solvent, or destruction of the microspheres, will suffice to separate out the marker isotope(s).

The stability in aqueous suspension has been evaluated for the following adverse conditions: 1) leaching of the isotopes into the aqueous medium during storage, and 2) reproducability of the signal obtained from the microspheres after prolonged storage. Each lot complies with the following specifications: 1) no loss of isotopes from microspheres after six months storage in aqueous medium; and 2) no change in stable-isotope-labeled signal during neutron activation analysis after six months storage in aqueous medium.

8.5 Color Coding Corresponding to the Stable Isotope with which the Microspheres are Marked Because microspheres marked with different stable isotopes are not thereby generally rendered visually distinguishable from another, the different stable-isotope-marked are preferably different dyed, thereafter supporting human visual recognition of, and distinction between, the differing species of marked microspheres.

In accordance with these and other possible variations and adaptations of the present invention the scope of the invention should be determined in accordance with the following claims, only, and not solely in accordance with that embodiment within which the invention has been taught.

What is claimed is:

1. A microsphere comprising:
   a uniform plastic body in the form of a microsphere marked with a predetermined amount of a non-radioactive stable isotope of an element which isotope and element can be rendered radioactive for detection by neutron activation analysis.

2. The marked microsphere according to claim 1
   wherein the plastic body in the form of the microsphere physically holds the element;
   wherein the marking is by physical association between the element and the microsphere.

3. The marked microsphere according to claim 1
   wherein the plastic body in the form of the microsphere chemically binds the element;
   wherein the marking is by chemical association between the element and the microsphere.

4. The marked microsphere according to claim 1
   wherein the plastic body in the form of the microsphere is marked with a plurality of non-radioactive stable isotopes.

5. The marked microsphere according to claim 1 deployed within a sample wherein the plastic body in the form of a microsphere is marked with an isotope that is so rare within material of the sample that essentially all detection counts during neutron activation analysis can be attributed to presence of the isotope, and essentially none result from the material of the sample.

6. The marked microsphere according to claim 1 marked with a plurality of isotopes that, following neutron activation analysis, are by their unique energy signatures upon decay from an excited state individually distinguishable from one another.

7. The marked microsphere according to claim 1 marked with an isotope that, following neutron activation analysis, produces a daughter nuclide having a half life ($t_{1/2}$) greater than one day.

8. The marked microsphere according to claim 1 marked with an isotope that, following neutron activation analysis, produces a daughter nuclide having a half life ($t_{1/2}$) less than two years.

9. The marked microsphere according to claim 1 marked with an isotope that, following neutron activation analysis, produces a daughter nuclide having a half life ($t_{1/2}$) of at least two days and shorter than one month.

10. The marked microsphere according to claim 1 marked with an element from the group consisting of
    gold, antimony, lanthanum, samarium, europium, terbium, holmium, ytterbium, lutetium, hafnium, tantalum, tungsten, rhenium, osmium, iridium, scandium and bromide.

11. The marked microsphere according to claim 1 color coded in accordance with the element with which it is marked.

12. The marked microsphere according to claim 1 used in blood flow analysis, the marked microsphere characterized in that it may be detected within a tissue sample resultant from blood flow analysis.

13. The marked microsphere according to claim 1 used in high-throughput screening for drug discovery and evaluation, the marked microsphere characterized in that it may be detected within a sample suitable for said high-throughput screening for drug discovery and evaluation.

14. The marked microsphere according to claim 1 comprising:
   a biodegradable microsphere body; with which is associated
   the non-radioactive stable isotope of an element only during the perpetuation of the physical microsphere body, the isotope being loosed when the body biodegrades.

15. The marked microsphere according to claim 14 wherein the biodegradable microsphere body consists essentially of a substance digestible in the gut of a higher animal.

16. The marked microsphere according to claim 1 wherein the plastic body in the form of the microsphere comprises:
   polystyrene.

17. The marked microsphere according to claim 1 wherein the plastic body is uniformly homogeneously marked.

18. The marked microsphere according to claim 17 wherein the spherical plastic body comprises:
   polystyrene.

19. A microsphere marked with a non-radioactive stable isotope of an element,
   which isotope and element can be rendered radioactive for detection by neutron activation analysis,
   wherein the isotope following neutron activation will generate a theoretical specific activity (s) of which exceeds $1 \times 10^{10}$ disintegrations per minute per kilogram of tracer, as appears in the equation for specific activity, s, induced in any parent nuclide during neutron activation:

$$s = 6.02 \times 10^{26} \phi \sigma f A^{-1} (0.5)^{t_1/t_{1/2}} [1-(0.5)^{t/t_{1/2}}]$$

where: s=specific activity in disintegrations per unit mass $(s^{-1}kg^{-1})$, $\phi$=flux of neutrons in $m^{-2}s^{-1}$, $\sigma$=cross-section for neutron interaction with parent nuclide ($m^2$), f=fractional abundance of the parent nuclide, A=atomic weight of the parent element, $t_1$=time between activation and counting (hours), t=activation period (hours), $t_{1/2}$=half-life of daughter nuclide (hours).

20. The marked microsphere according to claim 19 comprising:
   a spherical plastic body.

21. A microsphere comprising:
   a uniform plastic body in the form of a microsphere
   uniformly homogeneously marked with a predetermined amount of a non-radioactive stable isotope of an element which isotope and element can be rendered radioactive for detection by neutron activation analysis.

22. A microsphere marked with a non-radioactive stable isotope of an element the presence of which isotope which can be detected by neutron activation analysis,
   the isotope following neutron activation generating a theoretical specific activity (s) of which exceeds $1 \times 10^{10}$ disintegrations per minute per kilogram of tracer, as appears in the equation for specific activity, s, induced in any parent nuclide during neutron activation:

$$s = 6.02 \times 10^{26} \phi \sigma f A^{-1} (0.5)^{t_1/t_{1/2}} [1-(0.5)^{t/t_{1/2}}]$$

where: s=specific activity in disintegrations per unit mass $(s^{-1}kg^{-1})$, $\phi$=flux of neutrons in $m^{-2}s^{-1}$, $\sigma$=cross-section for neutron interaction with parent nuclide ($m^2$) f=fractional abundance of the parent nuclide, A=atomic weight of the parent element, $t_1$=time between activation and counting (hours), t=activation period (hours), $t_{1/2}$=half-life of daughter nuclide (hours).

* * * * *